US011331268B2

(12) United States Patent
Nguyen et al.

(10) Patent No.: US 11,331,268 B2
(45) Date of Patent: May 17, 2022

(54) TASTE MASKING PRODUCT

(71) Applicant: The University of Western Australia, Nedlands (AU)

(72) Inventors: Ngoc Minh Nguyen, Morley (AU); Lee Yong Lim, Willetton (AU)

(73) Assignee: The University of Western Australia, Nedlands (AU)

( * ) Notice: Subject to any disclaimer, the term of this patent is extended or adjusted under 35 U.S.C. 154(b) by 0 days.

(21) Appl. No.: 16/461,652

(22) PCT Filed: Nov. 17, 2017

(86) PCT No.: PCT/AU2017/051266
§ 371 (c)(1),
(2) Date: May 16, 2019

(87) PCT Pub. No.: WO2018/090096
PCT Pub. Date: May 24, 2018

(65) Prior Publication Data

US 2019/0350850 A1 Nov. 21, 2019

(30) Foreign Application Priority Data

Nov. 18, 2016 (AU) ............................... 2016904727

(51) Int. Cl.
| | |
|---|---|
| *A61K 9/00* | (2006.01) |
| *A61K 9/20* | (2006.01) |
| *A61K 31/138* | (2006.01) |
| *A61K 31/5517* | (2006.01) |
| *A61K 31/7056* | (2006.01) |
| *A23G 1/40* | (2006.01) |
| *A23G 1/42* | (2006.01) |
| *A23G 1/48* | (2006.01) |

(52) U.S. Cl.
CPC .............. *A61K 9/0056* (2013.01); *A23G 1/40* (2013.01); *A23G 1/42* (2013.01); *A23G 1/48* (2013.01); *A61K 9/205* (2013.01); *A61K 9/2009* (2013.01); *A61K 9/2013* (2013.01); *A61K 9/2018* (2013.01); *A61K 9/2031* (2013.01); *A61K 9/2068* (2013.01); *A61K 31/138* (2013.01); *A61K 31/5517* (2013.01); *A61K 31/7056* (2013.01); *A23V 2002/00* (2013.01)

(58) Field of Classification Search
CPC .............. A61K 9/0056; A61K 31/5517; A61K 9/2009; A61K 9/2018; A61K 9/205; A61K 9/2013; A61K 9/2068; A61K 31/138; A61K 31/7056; A61K 9/2031; A23G 1/48; A23G 1/40; A23G 1/42; A23V 2002/00
USPC ......................................................... 514/23
See application file for complete search history.

(56) References Cited

U.S. PATENT DOCUMENTS

| | | | |
|---|---|---|---|
| 586,504 A | 7/1897 | Marcsch | |
| 7,763,276 B1 | 7/2010 | Shodai et al. | |
| 2004/0191298 A1* | 9/2004 | Nicklasson | A61K 36/22 424/440 |
| 2007/0269493 A1 | 11/2007 | Lang | |
| 2007/0269558 A1 | 11/2007 | Lang | |
| 2010/0010101 A1* | 1/2010 | Cherukuri | A61K 9/1694 514/770 |
| 2013/0004604 A1 | 1/2013 | Davis | |
| 2014/0004604 A1 | 1/2014 | Schwartz et al. | |
| 2014/0142076 A1* | 5/2014 | Ahmed | A61K 9/2031 514/178 |

FOREIGN PATENT DOCUMENTS

| | | |
|---|---|---|
| DE | 202012009981 | 11/2012 |
| JP | 2004155781 | 6/2004 |
| WO | WO2004084865 A1 | 10/2001 |

OTHER PUBLICATIONS

Chavez-Pacheco et al., Development and Sedative Effect of a New Formulation of Midazolam in Chocolate Bars, Latin American Journal of Pharmacy, vol. 30(10):1977-1984, Nov. 2011.
Extended European Search Report dated May 4, 2020 issued in related European Patent Application No. 17872630.3.
Perez et al., "Development and Validation of a Method to Quantify Midazolam in a New Oral Formulation for Pediatric Use", American Journal of Analytical Chemistry, vol. 3:552-558, Aug. 2012.
Taj et al., "Taste Masked Orally Disintegrating Pellets of Antihistaminic and Mucolytic Drug: Formulation, Characterization, and in Vivo Studies in Human", International Scholarly Research Notes, 1-8, Oct. 2014.
ANZCA Media Release, "Chocolate and chewing gum: anesthetists lead the way in patient comfort", Nov. 18, 2015, retrieved on Dec. 18, 2017 from www.anzca.edu.au/documents/2015-choc-and-chewy-2.pdf.
Sohi et al., "Taste Masking Technologies in Oral Pharmaceuticals: Recent Developments and Approaches", Drug Development and Industrial Pharmacy, vol. 30(5):429-448, May 2004.
Abraham et al., "Taste masking of pediatric formulation: a review on technologies, recent trends and regulatory aspects", Int. J. Pharm. Sci., vol. 6(1):12-19, Jan. 2014.
Suzuki et al., "Development of oral acetaminophen chewable tablets with inhibited bitter taste", Int. J. Pharm,, vol. 251(1-2):123-32, Jan. 30, 2003.
International Search Report and Written Opinion issued on International Patent Application No. PCT/AU2017/051266, dated Dec. 13, 2017.
International Preliminary Report on Patentability issued on International Patent Application No. PCT/AU2017/051266, dated Mar. 7, 2019.
Demand for International Preliminary Examination with Proposed Amendments, filed on International Patent Application No. PCT/AU2017/051266, dated Sep. 13, 2018.

* cited by examiner

Primary Examiner — Yih-Horng Shiao
(74) Attorney, Agent, or Firm — Howson & Howson LLP; Colleen M. Schaller

(57) ABSTRACT

This invention relates to a chocolate or chocolate substitute composition or product comprising (a) at least compound to be delivered to a subject; (b) a chocolate or chocolate substitute matrix and at least (i) a masking agent or (ii) a firming agent, wherein the composition or product is substantially stable.

19 Claims, 15 Drawing Sheets

TASTE MASKING PRODUCT

CROSS-REFERENCE TO RELATED APPLICATIONS

This is a National Stage Entry under 35 U.S.C. 371 of International Patent Application No. PCT/AU2017/051266, filed Nov. 17, 2017, which claims priority to Australian Patent Application No. 2016904727, filed Nov. 18, 2016. These applications are incorporated by reference herein.

TECHNICAL FIELD

The present invention relates to a product, suitable for oral delivery, comprising a taste-masked product. It includes a method for the preparation of the product. The invention also relates to a chewable chocolate or chocolate substitute delivery system, and more particularly, to a chewable chocolate or chocolate substitute for the oral delivery of a pharmaceutical or a drug, and a method for manufacturing the same.

BACKGROUND ART

Dr. Harry Shirkey in 1963 famously proclaimed paediatric patients to be "therapeutic orphans" to draw attention to the dire lack of drug information and drug formulations for children. Since then, some progress has been made through legislations in the US and EU that either mandates or incentivizes drug trials in children. Nevertheless, 65%-80% of approved drugs today are still not tested in children, while more than 20% of medicines in Australia with paediatric dosage guidelines did not have child-friendly formulations. Where no suitable drug product is available at the point of care, commercial tablets, capsules or injections are manipulated by pharmacists or caregivers to produce appropriate oral doses, usually in liquid forms, for children. Such extemporaneous practices can be risky, since the lack of quality control measures can result in inaccurate dose, altered product efficacy or medication error. The end products are also often not sufficiently palatable, adding to poor medication adherence and sub-optimal therapeutic outcomes in paediatric patients.

Children reject medicines mainly because of poor taste and, for children below 6 years of age, the inability to swallow solid medicines, such as tablets and capsules. Up until recently, taste is not an evaluated parameter for paediatric drug formulations, despite its importance in influencing therapeutic compliance in children. The limited availability of solid dosage forms small enough to be swallowed by young children has compelled the World Health Organization to launch a global "Make medicines child size" campaign in 2007, and to advocate flexible solid oral dosage forms for children.

To achieve the benefits of a medicine, the patient must be willing to take it in the correct amount at the appropriate time. Most medicines are not formulated for use in children. For those that are, few are considered sufficiently palatable. Lack of palatability can be attributed to poor taste and, for children below 6 years, the inability to swallow solid medicines, such as tablets. Particular issues arise where medicines have a bitter or unpleasant taste.

Taste-masking techniques have been applied in the pharmaceutical industry to mask or overcome bitter or unpleasant tastes associated with active pharmaceutical ingredients/drugs to achieve patient acceptability and compliance. Oral administration of bitter or unpleasant tasting drugs is often the biggest barrier to achieve medication compliance for patient groups, such as paediatrics.

Unless the active ingredient is tasteless or does not have any unpleasant taste, taste-masking plays a key role in the success of a final solid oral dosage form. The efficiency of taste-masking is often a key determinant for the success of specialized dosage forms like orally disintegrating tablets and films, and chewable tablets.

Mechanisms of taste-masking rely on two major approaches: (a) to add sweeteners, flavours, and effervescent agents to mask the unpleasant taste; or (b) to avoid contact of bitter/unpleasant drugs with taste buds.

In recent times, significant progress has been made in the area of taste-masking by applying novel strategies and techniques, such as hot-melt extrusion and microencapsulation. There remains, however, a need in the paediatric and geriatric fields for a taste masking delivery system that can deliver bitter or unpleasant tasting active pharmaceutical ingredients/drugs to a patient.

A drug that falls into the field of bitter active pharmaceutical ingredients that is often difficult to deliver, at least to children, is midazolam. Midazolam is a highly effective oral sedative and pre-procedural medicine for children and adolescents. The lack of an oral commercial product in Australia has led local hospitals to administer extemporaneously prepared midazolam syrups which have a foul taste and are often rejected by the children. Inadequate sedation presents difficulties in children who are very anxious or uncooperative in the preoperative setting (e.g. children with autism). Uncooperative children have to be held down and restrained for the introduction of anaesthesia, which is traumatising for a child and the family. In adolescents, this can also pose significant safety risks for the attending staff.

Midazolam is commonly prescribed to children at an oral dose of 0.5 mg/kg, to a maximum dose of 15-20 mg, for sedation, seizures and premedication, prior to the induction of anaesthesia. Midazolam injections in the strengths of 1 and 5 mg/ml are on the Therapeutic Goods Administration register, but oral syrups are not marketed in Australia. The absence of a suitable oral product has led the local hospitals to dispense a 2.5 mg/ml midazolam syrup prepared by the WA Hospitals Central Pharmaceutical Manufacturing Facility (also known as Auspman) or administer the 5 mg/ml injection by the oral, buccal or intranasal route. Intranasal drops have poor acceptance amongst children and are rarely used. While the injection is routinely administered in the mouth as buccal drops in unconscious patients having seizures at home, the product does not have taste modifiers and is not well tolerated when administered orally to conscious patients. The high dose per ml of this product further causes grave concerns over safety should a wrong volume be measured and given. The only oral product in use in the perioperative setting is midazolam syrup, which has a foul taste. Not surprisingly, midazolam administration becomes a distressing experience for patients and their caregivers, who are already stressed out by the impending surgery, and safety and efficacy are compromised when some of the medicine is spat out or the child refuses subsequently to take any more of the medicine. Rejection of midazolam syrup presents particular difficulties in children who are very anxious or uncooperative in the preoperative setting (e.g. children with autism).

It is against this background that the present invention has been developed as a principal of general application. To this end, the inventors have ameliorated at least a deficiency in the field of compound delivery systems by developing a chocolate or chocolate substitute delivery system that masks the taste of certain compounds that are incorporated into the chocolate delivery system.

SUMMARY OF INVENTION

The present invention is directed to the development of at least a compound delivery system based upon chocolate or a chocolate substitute wherein the delivery system masks the taste of the certain compound(s) that are incorporated into the chocolate delivery system.

In one form, the invention resides in a delivery system and product that can be used to deliver active ingredients, drugs or pharmaceuticals to a person in need thereof. In this respect, the composition or product of the invention provides an alternative to liquid delivery systems or the use of buccal drops, at least for many bitter or unpleasant tasting compounds. In particular, it displays one or more of the following benefits:

(a) administration of a taste-masked composition or product potentially provides enhanced dosing accuracy with greater administration ease than the administration of liquids, which requires conscientious measurement of the prescribed dosing volumes. The dosing risk is amplified in unpalatable liquids due to their potential rejection by subjects and the accompanying stress induced in having to administer the unpalatable agent;

(b) the masked composition or product preferably softens in the mouth making the product chewable in the mouth, making it suitable for administration to even very young children who cannot swallow conventional tablets and capsules;

(c) the masked composition or product is preferably small and does not require water for administration; or (d) the familiarity of chocolate, coupled with the small size of the tablets, can be reassuring to a subject, in turn facilitating medication adherence.

According to a first embodiment, the invention resides in a chocolate or chocolate substitute composition or product comprising:

(a) at least a compound to be delivered to a subject;
(b) a chocolate or chocolate substitute matrix; and
(c) at least one of a (i) masking agent or (ii) suspending agent, wherein the composition or product is substantially stable.

A chocolate or chocolate substitute composition or product comprising:

(a) at least an active ingredient;
(b) a compound or dark chocolate or compound or dark chocolate substitute matrix;
(c) a masking agent that masks at least part of the taste of the ingredient in (a); and
(d) a suspending agent, wherein the composition or product (i) is prepared in the absence of water and (ii) is substantially stable at ambient temperature.

Preferably, the compound to be delivered is a bitter or unpleasantly tasting compound. Where the composition or product contains a suspending agent, the chocolate or chocolate substitute matrix will desirably provide a taste masking benefit to the composition or product. When the composition or product also includes a taste masking agent, that agent will preferably supplement or extend any taste masking effect of the chocolate or chocolate substitute matrix.

The compound to be delivered in the chocolate or chocolate substitute composition or product should be bioavailable when in a chocolate matrix. A compound will be bioavailable when in a chocolate matrix where it delivers the effect for which it is administered to the individual.

In one form, the chocolate or chocolate substitute composition or product is prepared in the absence of water and other aqueous vehicles, and is substantially stable.

According to a first form of the first embodiment, the invention resides in a chocolate or chocolate substitute composition or product comprising:

(a) at least an active ingredient;
(b) a chocolate or chocolate substitute matrix; and
(c) a masking agent that masks at least part of the taste of the ingredient in (a), wherein, the composition or product is (i) substantially stable, and (ii) the chocolate or chocolate substitute matrix supplements in part or in full the taste masking effect of the masking agent.

According to a second form of the first embodiment, the invention resides in a chocolate or chocolate substitute composition or product comprising:

(a) at least an active ingredient;
(b) a chocolate or chocolate substitute matrix; and
(c) a suspending agent, wherein, the composition or product is (i) substantially stable and (ii) the chocolate or chocolate substitute matrix masks part or all of the taste of the active ingredient in (a).

According to a third form of the first embodiment, the invention resides in a chocolate or chocolate substitute composition or product comprising:

(a) at least an active ingredient;
(b) a chocolate or chocolate substitute matrix;
(c) a masking agent that masks at least part of the taste of the ingredient in (a); and
(d) a suspending agent, wherein the composition or product is substantially stable.

According to a second embodiment, the invention resides in a chocolate or chocolate substitute composition or product comprising:

(a) at least a bitter or unpleasant tasting active pharmaceutical ingredient;
(b) a chocolate or chocolate substitute matrix;
(c) a taste-masking agent that masks at least part of the taste of the ingredient in (a), wherein the composition or product is substantially stable; and the taste-masking agent masks the bitter or unpleasant taste of the active pharmaceutical ingredient.

According to a third embodiment, the invention resides in a chocolate or chocolate substitute composition or product comprising;

(a) at least a bitter or unpleasant tasting pharmaceutical ingredient;
(b) a chocolate or chocolate substitute matrix; and
(c) a suspending agent wherein, (i) the composition or product is substantially stable, and (ii) the chocolate or chocolate substitute matrix masks part or all of the taste of the bitter or unpleasant tasting pharmaceutical ingredient.

According to a fourth embodiment, the invention resides in a chocolate or chocolate substitute composition or product comprising:

(a) at least a bitter or unpleasant tasting active pharmaceutical ingredient;
(b) a chocolate or chocolate substitute matrix;
(c) a taste-masking agent; and
(d) a suspending agent, wherein the composition or product is substantially stable; and the taste-masking agent masks the bitter or unpleasant taste of the active pharmaceutical ingredient.

According to a fifth embodiment, the invention resides in a method for preparing a chocolate or chocolate substitute composition or product produced according to the invention. Preferably, the method includes, without limitation, the steps of:

(a) preparing a chocolate liquor by blending the necessary ingredients for the desired type of chocolate,
(b) adding the active ingredient to the chocolate liquor,
(c) mixing the chocolate liquor with the active ingredient to achieve the desired taste and texture, and
(d) tempering the chocolate.

After tempering, the chocolate can be stored in large blocks for later processing, or moulded or formed into smaller pieces and individually wrapped.

In an alternate form of the above method, first the active ingredient may be combined with a masking and or a suspending agent. The combination is then combined with the chocolate or chocolate substitute and mixed for a period of time sufficient to ensure that a substantially homogeneous composition is formed. That time period will usually be at least 5 hours. Once a substantially homogenous liquid composition is formed, the mixture can be transferred to moulds and allowed to set.

According to a sixth embodiment, the invention provides a method for treating a subject, said method comprising the steps of: (a) preparing a product according the invention; and (b) administering an effective amount of the product to the subject. The effectiveness of the product will be determined by the effect that the active ingredient is to achieve. Thus, the amount of the product that will be administered or given to the subject will therefore be the amount of active ingredient required to at least deliver that effect.

According to a seventh embodiment of the invention, there is provided a method of treating a subject with an ailment or a condition, said method comprising the steps of: administering to the subject a therapeutically effective amount of, (i) a chocolate or chocolate substitute composition or product as describe herein, or a (ii) chocolate or chocolate substitute composition or product produced by a method of the invention.

According to an eighth embodiment, the invention resides in the form of a chocolate or chocolate substitute liquid or beverage prepared by fluidizing the chocolate or chocolate substitute composition or product of the invention described herein.

Additional objectives, advantages and novel features will be set forth in the description which follows or will become apparent to those skilled in the art upon examination of the drawings and the ensuing detailed description of several non-limiting embodiments which follows.

BRIEF DESCRIPTION OF THE DRAWINGS

The disclosure will provide details in the following description of preferred embodiments with reference to the following figures wherein.

DETAILED DESCRIPTION OF THE INVENTION

Figure 1:
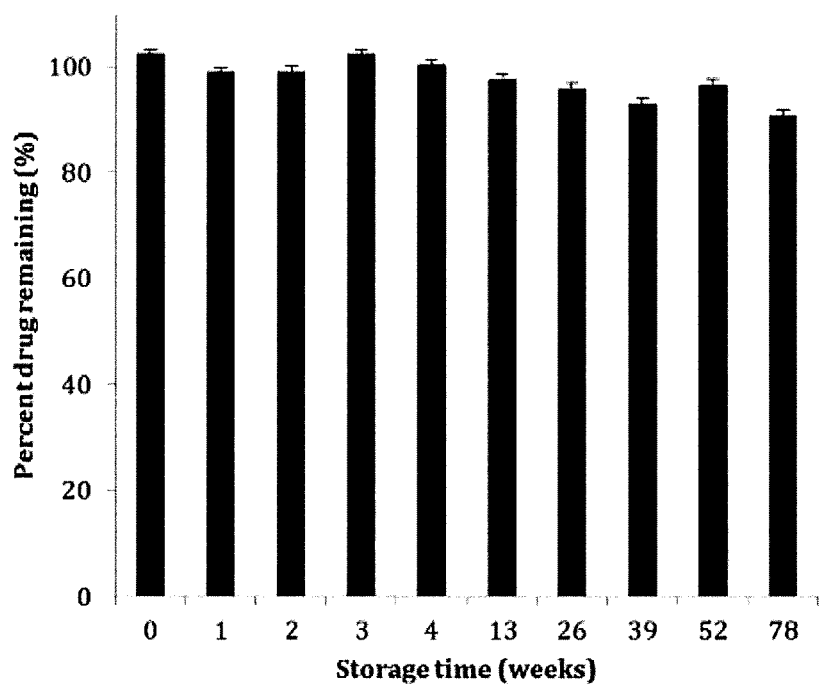
FIG. 1 presents the percent drug remaining in midazolam chocolate tablets following storage at ambient temperature over 18 months. Data represents mean±SD (n=3).

The present invention is directed to a composition or product and a related method for its preparation, wherein the composition or product is adapted to mask the taste of a compound(s) in the composition or product. Taste masking can be defined as the perceived reduction of an undesirable taste commonly associated with a particular compound, such as a pharmaceutical.

General Observations

The present invention is not to be limited in scope by the following specific embodiments. This detailed description is intended for the purpose of exemplification only. Functionally equivalent products, compositions and methods are within the scope of the invention as described herein. Consistent with this position, those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

In this document, the term 'bitter" is used to describe a compound that induces a basic taste sensation that is acrid, astringent, harsh or disagreeable to a subject or subjects likely to receive the compound. Such a compound might, for example, have a sharp, pungent taste that is not sweet.

As used herein an "active ingredient" is one that has or provides a biological or diagnostic effect or benefit when administered to a subject (including humans). The effect or benefit of the ingredient need not be therapeutic, it may be of any biological effect that is desired or any diagnostic benefit or effect that is required. For example, the ingredient may be, by way of illustration only, a vitamin, mineral, nutrient, pharmaceutical ingredient, non-pharmaceutical compound, Chinese traditional medicines (such as leaves, bark, roots, berries, flowers, and animal parts) or indigenous medicines, a biological marker or diagnostic detection system.

As used herein "substantially stable" means that the composition or product is capable of being stored for at least 4 months, more preferably at least 6 months while still preserving greater than 70% activity, more preferably still preserving greater than 80% activity of the compound being delivered to a subject. For example, a composition or product is 'substantially stable' if that composition or product delivers at least 70% and more preferably 71, 72, 73, 74, 75, 76, 77, 78, 79, 80, 81, 82, 83, 84, 85, 86, 87, 88, 89, 90, 91, 92, 93, 94, 95, 96, 97, 98 or 99% of the activity that it was originally prepared to deliver, after at least one of 4, 5, 6, 7, 8, 9, 10, 11, 12, 13, 14, 15, 16, 17, 18, 19, 20, 21, 22, 23 or 24 months.

The term "therapeutically effective amount" as used herein includes within its meaning a non-toxic but sufficient amount of a compound or composition for use in the invention to provide the desired therapeutic effect. What constitutes a therapeutic effective amount will depend in the subject being treated and the potency and bioavailability of the pharmaceutical or drug. For example, the exact amount of therapeutic compound required to treat a subject will vary from subject to subject depending on factors such as the species being treated, the age, weight and general condition of the subject, co-morbidities, the severity of the condition being treated, the particular compound being administered and the mode of administration and so forth. Thus, for any given case, an appropriate "effective amount" may be determined by one of ordinary skill in the art using only routine methods.

In this document, the use of the singular includes the plural unless specifically stated otherwise. Also, the use of "or" means "and/or" unless stated otherwise. Furthermore, the use of the term "including", as well as other forms, such as "includes" and "included", is not limiting.

As used herein the term "subject" includes, without limitation a human or non-human, such as an individual of any species of social, economic or research importance including but not limited to lagomorph, ovine, bovine, equine, porcine, feline, canine, primate and rodent species. Although it will be understood to include all of these species, the term is preferentially referring to humans and more particularly to those treated by the medical disciplines of paediatrics and geriatrics.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Throughout this specification, unless the context requires otherwise, the word "comprise", or variations such as "comprises" or "comprising", will be understood to imply the inclusion of a stated integer or group of integers but not the exclusion of any other integer or group of integers.

The invention described herein may include one or more range of values (for example, size, displacement and field strength etc.). A range of values will be understood to include all values within the range, including the values defining the range, and values adjacent to the range that lead to the same or substantially the same outcome as the values immediately adjacent to that value which defines the boundary to the range. For example, a person skilled in the field will understand that a 10% variation in upper or lower limits of a range can be totally appropriate and is encompassed by the invention. More particularly, the variation in upper or lower limits of a range will be 5% or as is commonly recognised in the art, whichever is greater.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Illustrative Non-Limiting Embodiments of the Invention

According to a first embodiment, the invention resides in a chocolate or chocolate substitute composition or product comprising:
  (a) at least a compound to be delivered to a subject;
  (b) a chocolate or chocolate substitute matrix; and
  (c) at least one of a (i) masking agent or (ii) suspending agent,
wherein the composition or product is substantially stable.

Preferably, (1) the delivered compound that is identified by (a) is a bitter or unpleasantly tasting compound and (ii) the chocolate or chocolate substitute composition masks part or all of the taste of the compound of (a).

According to the invention, the composition or product described herein will be substantially stable, in that, it is capable of being stored for at least, 4, 5, 6, 7, 8, 9, 10, 11, 12, 13, 14, 15, 16, 17, 18, 19, 20, 21, 22, 23 or 24 months while still preserving greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent of the activity of the compound being delivered by the invention.

Over time the stability of a composition or product will be expected to generally decrease. As such, where the composition or product is stored for periods of greater than 12 months, the activity of the composition or product can be reduced to within the range of 70 to 99% activity. Such storage will still be regarded as a substantially stable product produced according to the invention. Where storage is greater than 12 months one should expect to see some reduction in percent activity. For example, the activity can be reduced by about 4, 5, 6, 7, 8, 9, 10, 11, 12, 13, 14, 15, 16, 17, 18, 19, 20 percent. Preferably, the activity is reduced by no more than about 5 to 10 percent after 12 months.

Stability can be influenced by numerous factors. One of those factors is light exposure. Where a compound(s) to be delivered to a subject is light sensitive, the compound should be stored away from direct light, by for example, wrapping the composition or product in foil or some other form of wrapping that prevents direct light exposure.

Another factor that can influence stability, particularly in the case of chocolate or chocolate substitute products is heat. When assessing stability, the composition or product should not be subjected to excessive heat treatment. In this respect, the chocolate or chocolate substitute composition or product should be stored preferably below 30 degrees Celsius. Ideally, the composition or product is stored below 29, 28, 27, 26, 25, 24, 23, 22, 21, 20 degrees Celsius. Ordinarily, the composition or product will be stored at room temperature or less. Such temperatures include, without limitation, 19, 18, 17, 16, 15, 14, 13, 12, 11, 10, 9, 8, 7, 6, 5, 4, 3, 2, 1 degree Celsius or in a colder environment.

When chocolate as compared to a chocolate substitute matrix is used in the invention, the chocolate is preferably a chocolate prepared without cocoa butter. Examples of such a chocolate include, compound chocolate or dark chocolate. The chocolate used in the invention is preferably prepared by combining cocoa with vegetable fat, usually tropical fats and/or hydrogenated fats, as a replacement for cocoa butter.

Chocolate used in the invention will have at least 40% cocoa mass. In this respect, the chocolate may include at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% cocoa mass. Preferably, the chocolate possesses cocoa percentages ranging from 40% to 99%. Most preferably, the chocolate possesses cocoa percentages ranging from 55 to 80%.

Where a chocolate substitute is used in the invention, the substitute is preferably carob or cocoa powder. Where carob is used as the chocolate substitute matrix, the carob will have at least 40% carob mass. In this respect, the carob may include at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% carob mass. Preferably, the chocolate substitute composition or product possesses carob percentages ranging from 40% to 99%. Most preferably the chocolate substitute possesses carob percentages ranging from 55 to 80%.

In the composition or product of the invention, the amount of chocolate or chocolate substitute present will be at least 50 percent of the total weight of the composition or product. Those skilled in the art will recognize that the amount of chocolate used in the composition or product will vary depending on the amount of cocoa or substitute present and the taste of the compound to be delivered to the subject. In that respect, the chocolate or chocolate substitute may be at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% of the total weight of the composition or product. Preferably, the chocolate or chocolate substitute in the composition or product ranges from 55% to 85%. Most preferably the chocolate or chocolate substitute in the composition or product ranges from 70 to 80%.

A compound that can be delivered to a subject with the present invention, will include any compound or compounds that a subject might require to alter or ameliorate a condition, or treat a state, within that subject. Where the compound is used to alter or ameliorate a condition, or treat a state, that compound will at least ameliorate a deficiency or in some cases treat or ameliorate an excess of a particular compound in a subject. To achieve this effect, the compound(s) will be present in the composition in an amount that is capable of delivering a benefit to the subject. This must be determined having regard to the compound to be delivered and the levels that are deemed safe within a subject. Those skilled in the art of delivering a compound will understand what those levels should be.

In an alternate for the invention the compound is one that the subject might need to permit or facilitate a diagnostic or prognostic assessment of a condition or ailment in the subject.

Compounds that might be administered in the composition or product of the invention include, without limitation, vitamins, minerals, nutrients, traditional medicines (such as Chinese traditional medicine) pharmaceutical ingredients and or other drugs as well as other non-pharmaceutical compounds such as bitter herbal medicines that a subject may require or desire for health and well-being. Desirably, the compound is a bitter or unpleasant tasting active pharmaceutical ingredient and or drug.

As the amount of compound to be delivered to a subject increases or decreases, those skilled in the art will realize that the amount of chocolate or chocolate substitute in the composition or product may also be increased or decreased to mask the taste or flavour of the additive compound. In an alternate form, the amount of chocolate or chocolate substitute in the composition or product may not increase or decrease but, the cocoa mass or substitute mass (e.g. carob) in the chocolate or chocolate substitute may be varied.

A central challenge of administering medicine to children and the geriatric is a matter of taste—many drugs, by their very nature, often taste unpleasant, with bitter taste a primary culprit. A drug's taste and palatability is one of the biggest barrier to completing treatment.

According to a first form of the first embodiment, the invention resides in a chocolate or chocolate substitute composition or product comprising:
  (a) at least an active ingredient;
  (b) a chocolate or chocolate substitute matrix; and
  (c) a masking agent that masks at least part of the taste of the ingredient in (a),
wherein, the composition or product is (i) substantially stable, and (ii) the chocolate or chocolate substitute matrix supplements in part or in full the taste masking effect of the masking agent.

When present the masking agent(s) constitutes about 0.1% to 25% dry weight of the final composition. In this respect the masking agent(s) constitute about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, 6.5, 7, 7.5, 8, 8.8, 9, 9.5 10, 10.5, 11, 11.5, 12, 12.5, 13, 13.5, 14, 14.5, 15, 15.5, 16, 16.5, 17, 17.5, 18, 18.8, 19, 19.5, 20, 20.5, 21, 21.5, 22, 22.5, 23, 23.5, 24 or 24.5% dry weight of the final composition. Preferably the masking agent(s) constitutes about 1% to 20% dry weight of the final composition.

The masking agent may also serve to provide a suspending activity of the compound to be delivered to the subject. Thus, the masking agent may deliver more than one activity to the formulation of the product or the composition. Ideally, such an agent will be recognized for, and by, its primary activity, but its dual purpose use will be taken into account during product and composition development.

In an embodiment, there may be more than one masking agent present in the composition or product wherein, each agent may be present as about 0.1% to 10% of the dry weight of the final composition.

A particularly effective class of compounds that can function as bitterness masking agents are hydrogenated, ethoxylated glycerol esters. These types of compounds are commercially available and may be formed in a well-known manner, namely by the ethoxylation of glycerol. One commercially available compound which works as a bitter masking agent and has suspending properties is sold by the BASF Company under the trade name CREMOPHOR®, including CREMOPHOR® 40 and CREMOPHOR® 60 hydrogenated ethoxylated castor oils. Other suitable bitterness masking agents or taste blockers that can be used in the invention include, but are not limited to: adenosine 5'-monophosphate, thymidine 5' monophosphate, adenosine 5' diphosphate, adenosine 3' monophosphate, adenosine 5'-succinate, adenosine 5' triphosphate, adenosine 2' monophosphate, 5'-cytidylic acid and inosinic acid.

Some alternate commercially available bitterness masking agents or taste blockers that can be used in the invention include, but are not limited to: Ottens BITTERNESS BLOCKERS® NI-1915-A and Firmenich SWEETNESS ENHANCER® 598960 TP 1054, Quest NATURAL BITTER BLOCKERS®, Fontarome MAG-NIFIQUE®, Givaudan MASKING FLAVOR®, WILD FAE®, GSB Natural Soy Masking Flavor (Milk Type) P.F. #8236, GSB Natural Sweetness Masking Flavor W.S. #7895, GSB Natural Masking Agent Flavor W.S. #5206, GSB Natural Masking Flavor W.S. #6500, GSB Natural Sugar Extender Type Flavor W.S. #8490, Mother Murphy NAT. MASKING TYPE FLAVOR 188505, Mother Murphy NAT. MASKING FLAVOR 155122, Mother Murphy NAT. BITTER MASKING FLAVOR 2111197, Mother Murphy N&A MASKING FLAVOR, W.S. 2110085, Taste Advantage Natural Flavor-Mouthfeel Enhancer Type 1 in EtOH, Biogapress™ Vegetal BM 297 ATO Glyceryl dipalmitostearate, Glycerol monostearate (type I) EP, Mono and diglycerides NF, Precirol® ATO 5 Glycerol distearate (type I) EP, Glyceryl distearate NF, and combinations thereof.

According to a second form of the first embodiment, the invention resides in a chocolate or chocolate substitute composition or product comprising:
  (a) at least an active ingredient;
  (b) a chocolate or chocolate substitute matrix; and
  (c) a suspending agent,
wherein, the composition or product is (i) substantially stable and (ii) the chocolate or chocolate substitute matrix masks part or all of the taste of the active ingredient in (a).

The suspending agent, when present in the invention, enhances the suspension of the delivered compound within the chocolate or chocolate substitute matrix. Such an agent can also aid in firming the compound to be delivered to the subject and or enhancing taste sensation. One such agent that is particularly beneficial in the manufacture of the invention is xanthum gum. This compound helps to provide structure to the matrix, it is a suspending agent (i.e. it helps to suspend insoluble particles in the matrix) and in the mouth; the hydration of xanthum gum also helps to provide a creamy mouth feel, i.e. it is a taste enhancer.

When xanthum gum is present it is included at levels of about 0.01 to 10 percent weight based on the total weight of the composition or product. Preferably xanthum gum is present at levels of about 0.01, 0.05, 0.1, 0.15, 0.2, 0.25, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.5, 2, 2.5, 3, 3.5, 4, 4.5, 5, 5.5, 6, 6.5, 7, 7.5, 8, 8.8, 9 and 9.5 percent weight based on the total weight of the composition or product.

Alternate products that can be used as a replacement for xanthum gum include, without limitation: alginates, acacia, pectin, methylcellulose, hydroxyethylcellulose, carboxy methylcellulose, sodium carboxymethyl cellulose, tragacanth, guar gum, carageenan, gelatin, colloidal silicon dioxide, Chia Seeds, Flaxseed, Arrowroot powder, Cornstarch, Agar-Agar, Locust Bean Gum, Gum Arabic, Konjac root powder, Psyllium fibre. Such compounds will, however, only be suitable as a substitute for xanthum gum if they provide structure to the matrix, or act as a suspending agent and or taste enhancing agent. Alternatives as taste enhancers include, without limitation, pectin, soluble celluloses, gellan, guar gum, and Konjac root powder.

According to a preferred form of the first embodiment there is presented a chocolate or chocolate substitute composition or product comprising:
  (a) at least compound to be delivered to a subject;
  (b) a chocolate or chocolate substitute matrix;
  (c) a masking agent; and
  (d) a suspending agent,
wherein the composition or product is substantially stable.

Preferably in this form of the invention the masking agent is present in an amount of about 5 to 20 percent dry weight of the final composition and the suspending agent is present in an amount of about 0.01 to 10 percent dry weight of the final composition.

In yet a particularly preferred form of the invention, the composition or product can also include a firming agent, which when present will provide structure to the chocolate or chocolate substitute matrix. Such an agent may also display surfactant properties to assist in emulsifying or solubilizing the added compound in the chocolate or chocolate substitute matrix. Those familiar with the development of food based products will be familiar with the broad range of possible agents that may be added to a food based product or composition to assist in firming the composition or product.

Agents that are capable of adding a structure to the matrix as firming agent, which also deliver emulsifying or solubilizing affects to the added compound to be delivered to a subject, include for example, polyethylene glycol (PEG) (such as PEG 1450), gelatin and others, including water-soluble polymers such as methylcellulose, hydroxypropyl methylcellulose, and others.

When a firming agent is present it will be present at between about 5% to 25% dry weight of the final composition. In this respect, the firming agent preferably constitutes about 5, 5.5, 6, 6.5, 7, 7.5, 8, 8.8, 9, 9.5 10, 10.5, 11, 11.5, 12, 12.5, 13, 13.5, 14, 14.5, 15, 15.5, 16, 16.5, 17, 17.5, 18, 18.8, 19, 19.5, 20, 20.5, 21, 21.5, 22, 22.5, 23, 23.5, 24 or 24.5% dry weight of the final composition.

According to yet another preferred form of the first embodiment there is presented a chocolate or chocolate substitute composition or product comprising:
(a) at least compound to be delivered to a subject;
(b) a chocolate or chocolate substitute matrix;
(c) a masking agent;
(d) a firming agent; and
(e) a suspending agent,
wherein, the composition or product is substantially stable.

Preferably, the masking agent is present in an amount of about 5 to 20 percent dry weight of the final composition, the firming agent is present in an amount of about 5 to 25 percent dry weight of the final composition and the suspending agent is present in an amount of about 0.01 to 10 percent dry weight of the final composition.

In an illustrative form of the invention, there is presented a chocolate or chocolate substitute composition or product comprising:
(a) at least compound to be delivered to a subject;
(b) a chocolate or chocolate substitute matrix;
(c) a Cremophor (such as Cremophor RH40);
(d) xanthum gum; and
(e) PEG (such as PEG 1450),
wherein, the composition or product is substantially stable.

Preferably, the Cremophor is present in an amount of about 5 to 20 percent dry weight of the final composition, xanthum gum is present in an amount of about 0.01 to 10 percent dry weight of the final composition and the PEG is present in an amount of about 5 to 25 percent dry weight of the final composition.

The composition or product of the invention may also include natural and/or artificial flavours, additives, colours, and preservatives.

Preferably, the composition or product is also prepared in the absence of water. Chocolate contains fats. When water is added to chocolate, it is emulsified with the fats; the resultant product being unlike chocolate. The presence of water can also enhance drug instability and microbial growth.

Ideally, the invention resides in an edible, chewable composition or product present in the form of a moulded or formed solid compound or dark chocolate. The invention is also provided as an oral dosage form that may be a tablet, a wafer, a chewable tablet, a buccal tablet, a sub-lingual tablet or a gum.

A chocolate tablet can also be rendered into a liquid form by melting with warm water (2 ml of water to every tablet) to give an oral liquid for administration to e.g. very young children who can only take liquid products. The volume of warm water can be varied. In the instant application 2 ml of water was used for the midazolam tablet (prepared using the 500 mg mould) to simulate the volume of saliva for the animal taste experiment. This volume can be increased up to 10 ml per tablet or be any volume between about 2 ml and 10 mls (eg 2, 2.5, 3, 3.5, 4, 4.5, 5, 5.5, 6, 6.5, 7, 7.5, 8, 8.5, 9, 9.5, 10 mls) as it will facilitate faster melting of the tablet, and the less viscous product will aid in swallowing. 10 ml is suggested as it is within the capacity of a tablespoon. Certainly, a volume larger than 2 ml would be required if the chocolate tablet is larger e.g. the clindamycin chocolate tablet (1 g mould).

According to a second embodiment, the invention resides in a chocolate or chocolate substitute composition or product comprising:
(a) at least a bitter or unpleasant tasting active pharmaceutical ingredient;
(b) a chocolate or chocolate substitute matrix; and
(c) a taste-masking agent that masks at least part of the taste of the ingredient in (a),
wherein the composition or product is substantially stable; and the taste-masking agent masks the bitter or unpleasant taste of the active pharmaceutical ingredient.

According to a third embodiment, the invention resides in a chocolate or chocolate substitute composition or product comprising:
(a) at least at least a bitter or unpleasant tasting pharmaceutical ingredient;
(b) a chocolate or chocolate substitute matrix; and
(c) a suspending agent
wherein, (i) the composition or product is substantially stable, and (ii) the chocolate or chocolate substitute matrix masks part or all of the taste of the bitter or unpleasant tasting pharmaceutical ingredient.

According to a fourth embodiment, the invention resides in a chocolate or chocolate substitute composition or product comprising:
(a) at least a bitter or unpleasant tasting active pharmaceutical ingredient;
(b) a chocolate or chocolate substitute matrix;
(c) a taste-masking agent; and
(d) a suspending agent,
wherein the composition or product is substantially stable; and the taste-masking agent masks the bitter or unpleasant taste of the active pharmaceutical ingredient.

In a preferred form of the second to fourth embodiments, the bitter or unpleasant tasting active pharmaceutical ingredient and or drug is selected from the group consisting of sedatives and anxiolytics (such as midazolam), analgesics, antibiotics, antiparasitic, antiviral and anti-inflammatory drugs. Examples of such ingredients include, but are not limited to, ibuprofen, acetaminophen, dapsone, dexamethasone, diphenhydramine, enalapril, fentanyl citrate, antiparasitics (e.g. praziquantel), antivirals (e.g. ritonavir), haloperidol, hydrocortisone, morphine, prednisone (prednisolone), promethazine, thiamine, thiouracil, topimarate, clindamycin and tramadol, their salts and derivatives. Alternatively, the bitter or unpleasant tasting active pharmaceutical ingredient can be a traditional medicine e.g. herbs like wormwood has a strong antiparasitic that is known to be highly bitter.

For HIV treatment, ritonavir will have to be prepared with lopinavir (non-bitter).

Where the composition or product includes one or more of the above identified active pharmaceutical ingredients or drugs, the ingredient or drug will be present in the composition or product in a therapeutically effective amount.

Where the drug is midazolam or a salt thereof, the midazolam (or its salt) will be present in the composition or product in an amount of about 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.5 to 2 percent weight based on the total weight of the composition or product. In the illustrative example provided herein midazolam is included in the composition of the invention in an amount of 0.88% percent weight based on the total weight of the composition.

Where the drug is tramadol or a salt thereof, the tramadol (or its salt) will be present in the composition or product in an amount of about 1.3, 1.4, 1.5, 1.51, 1.52, 1.53, 1.54, 1.55, 1.56, 1.57, 1.58, 1.59, 1.6, 1.61, 1.62, 1.63, 1.64, 1.65, 1.66, 1.67, 1.68, 1.69, 1.7, 1.71, 1.72, 1.73, 1.74, 1.75, 1.76, 1.77, 1.78, 1.79, 1.8, 1.81, 1.82, 1.83, 1.84, 1.85, 1.86, 1.87, 1.88, 1.89, 1.9, 1.91, 1.92, 1.93, 1.94, 1.95, 1.96, 1.97, 1.98, 1.99, 2, 2.5 to 4 percent weight based on the total weight of the composition or product. In the illustrative example provided herein tramadol or a salt thereof is included in the composition of the invention in an amount of 1.88% percent weight based on the total weight of the composition.

As the therapeutically effective amount of the product to be delivered to the subject increases or decreases, those skilled in the art will realize that the amount of chocolate or chocolate substitute in the composition or product may be increased or decreased to mask the taste or flavour of the additive agents. In an alternate form, the amount of chocolate or chocolate substitute in the composition or product may not increase or decrease but the cocoa mass or substitute mass (e.g. carob) in the chocolate or chocolate substitute may be varied.

The chocolate or chocolate substitute in the composition or product of the invention may also include one or more active ingredients that vary in the type and relative weight of the ingredients, with the only limitation being that the chocolate retains its flavour, appearance, texture, and smoothness, and that the active ingredient and any other supplemental ingredients be uniformly distributed throughout the composition or product.

The present invention can include any of the wide variety of excipients commonly used in making pharmaceutical preparations and as such is not to be limited to any specific set of excipients. Suitable pharmaceutical excipients include but are not limited to, polymers, resins, plasticizers, fillers, binders, lubricants, glidants, disintegrants, solvents, co-solvents, colouring agents, buffer systems, surfactants, preservatives, sweetening agents, flavouring agents, pharmaceutical grade dyes or pigments, and viscosity agents, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, lactose, mannitol, sorbitol, tribasic calcium phosphate, dibasic calcium phosphate, compressible sugar, starch, calcium sulfate, dextro and microcrystalline cellulose, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose, and the like.

The edible composition may also include a carbohydrate. The carbohydrate adds nutritional benefits to the composition and may be desirable for children. The carbohydrate may constitute about 1% to about 25% dry weight of the final composition, or about 5% to about 20% dry weight of the final composition, or about 8% to about 18% dry weight of the final composition. For example, the carbohydrate may constitute 1, 2, 3, 4, 5, 6, 7, 8, 9, 10, 11, 12, 13, 14, 15, 16, 17, 18, 19, 20, 21, 22, 23, 24 or 25% dry weight of the final composition.

Suitable carbohydrates include, but are not limited to, wheat flour, flour, dextrin, maltodextrin, carboxymethylcellulose, methylcellulose. hydroxypropylmethylcellulose, guar gum, locust bean gum, carrageenan, algins, levan, elsinan, pullulan, pectins, chitosan, and gum arabic; native starches such as corn starch, waxy maize starch, high-amylose corn starch, potato, tapioca, rice and wheat starch, modified starches such as those that have been acid modified, bleached, oxidized, esterified, etherified, and combinations thereof.

Sweetening agents may also be used in the edible compositions. The sweetening agents may include, by way of illustration: sugar sweeteners and/or sugarless sweeteners, including high intensity artificial sweeteners. The sugar sweeteners generally include saccharide-containing components including, but not limited to, sucrose, dextrose, maltose, dextrin, invert sugar, fructose, levulose, galactose, corn syrup solids, vanilla syrup, and the like, alone or in any combination. Sugarless sweeteners include, but are not limited to sugar alcohols, such as sorbitol, mannitol, miraculim, xylitol, isomalt, hydrogenated starch hydrolysates, maltitol, steviol glycosides and the like, alone or in any combination. The high intensity artificial sweeteners include, but are not limited to, sucralose, aspartame, N-substituted APM derivatives such as neotame, salts of acesulfame, alitame, saccharin and its salts, cyclamic acid and its salts, glycyrrhizin and its salts, dihydrochalones, thaumatin, monellin, maltol, and the like, alone or in any combination. Combinations of sugar and/or sugarless sweeteners may be used in the product in any suitable amount. In one embodiment, the sweetening agent constitutes about 0.1% to about 20%, or about 2% to about 15% dry weight of the final composition. For example, the sweetening agent may constitute 0.1, 0.2, 0.3, 0.4, 0.5, 0.6, 0.7, 0.8, 0.9, 1 2, 3, 4, 5, 6, 7, 8, 9, 10, 11, 12, 13 14, 15, 16, 17, 18, 19, 20, 21, 22, 23, 24 or 25% dry weight of the final composition.

Flavourants may also be used to improve the flavour of the composition and, as with the sweeteners, the pleasant flavour of the flavourant is not altered or reduced by the taste-masking component of the present invention. Flavourants may be used singly or in combination. Flavourants may be both natural and synthetic flavours. Examples of preferred flavourants include, but are not limited to, sodium chloride, orange, cherry, strawberry, grape, cream, vanilla, chocolate, mocha, aniseed, eucalyptus, 1-menthol, carvone, anethole, citrus oils, essential oils such as peppermint, spearmint, or methyl salicylate (oil of wintergreen), cola, and the like.

In a highly preferred form of the fourth embodiment there is presented a chocolate or chocolate substitute composition comprising:

(a) a sedative or anxiolytic anaesthetic or a tranquilizer;
(b) a chocolate matrix;
(c) a masking agent; and
(d) a suspending agent, wherein, the composition or product is substantially stable.

More specifically, there is presented a chocolate or chocolate substitute composition or product comprising (a) a sedative or anxiolytic;
(b) a chocolate or chocolate substitute matrix;
(c) a masking agent; and
(d) a suspending agent, wherein, the composition or product is substantially stable.

In this specific form of the invention the masking agent can be present in an amount of about 5 to 20 percent dry weight of the final composition and the suspending agent can be present in an amount of about 0.01 to 10 percent dry weight of the final composition.

In yet another specific form of the invention, the composition or product can also include a firming agent, which when present will provide structure to the chocolate or chocolate substitute matrix. Such an agent may also display surfactant properties to assist in emulsifying or solubilizing the added compound in the chocolate or chocolate substitute matrix. Those familiar with the development of food based products will be familiar with the broad range of possible agents that may be added to a food based product or composition to assist in firming the composition or product.

For example, the invention provides a chocolate or chocolate substitute composition or product comprising:

(a) a sedative or anxiolytic (such as midazolam);
(b) a chocolate or chocolate substitute matrix;
(c) a Cremophor (such as Cremophor RH40);
(d) xanthum gum; and
(e) a PEG (such as PEG 1450), wherein, the composition or product is substantially stable.

Preferably, the Cremophor is present in an amount of about 5 to 20 percent dry weight of the final composition, xanthum gum is present in an amount of about 0.01 to 10 percent dry weight of the final composition and the PEG is present in an amount of about 5 to 25 percent dry weight of the final composition.

Preferably, the sedative or anxiolytic is midazolam more specifically midazolam hydrochloride present in an amount of about 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.5 to 2 percent weight based on the total weight of the composition or product.

Midazolam chocolate tablets of the invention are believed to provide a superior alternative to the current midazolam oral syrup and buccal drops based on the following reasons: (1) Administration of the chocolate tablet provides higher dosing accuracy with greater ease than the administration of liquids, which requires conscientious measure of the pre- scribed dosing volumes. The dosing risk is amplified in unpalatable liquid medicines due to their potential rejection by young patients and the accompanying stress induced in caregivers having to administer the foul medicines; (2) The chocolate tablet is chewable in the mouth, making it suitable for administration to even very young children who cannot swallow conventional tablets and capsules; (3) The choco- late tablet is small and does not require water for adminis- tration, making it appropriate for use pre-procedurally and for the induction of anaesthesia; (4) The familiarity of chocolate, coupled with the small size of the tablets, can be reassuring to a sick child, in turn facilitating medication adherence.

Midazolam chocolate tablets also provide for flexible dosing, an advantage associated with liquid formulations that is not often achievable safely with conventional tablets and capsules. With the chocolate tablets, dose escalation is possible by taking multiple chocolate tablets, all of which is simply chemable in the mouth. If a dose smaller than 5 mg is required, the pliable chocolate tablets can be readily cut along the score lines into halves or quarters to provide the appropriate dose.

Compared with bulky liquid formulations, the chocolate formulations are more convenient and cheaper to store, transport and administer. Moreover, the chocolate tablets of the invention are formulated without the addition of water, unlike another known chocolate formulation of midazolam which uses the midazolam injection as the drug source. Water is known to be incompatible with chocolate manu- facture, causing either phase separation or phase inversion. The absence of added water in our tablets will provide greater storage stability not only to the chocolate base, but also to any incorporated drug, particularly labile drugs, than liquid formulations. To date, the inventors have stored chocolate midazolam products produced according to the invention for at least 18 months at ambient temperature without apparent deleterious effects.

According to a fifth embodiment there is provided a method of preparing a chewable chocolate or chocolate substitute composition produced according to the invention. The method includes, without limitation, the steps of:
(a) preparing a chocolate liquor by blending the necessary ingredients for the desired type of chocolate,
(b) adding the active ingredient to the chocolate liquor,
(c) mixing the chocolate liquor with the active ingredient to achieve the desired taste and texture, and
(d) tempering the chocolate.

After tempering, the chocolate may be stored in large blocks for later processing, or moulded or formed into smaller pieces and individually wrapped.

An advantage of the techniques used in practicing the present invention is that one can produce a uniform distri- bution of the active ingredient in the delivery product.

In an alternate form of the above method, first the active ingredient may be combined with a masking and or a firming agent. The combination is then combined with chocolate or chocolate substitute and mixed for a period of time sufficient to ensure that a substantially homogeneous composition is formed. That time period will usually be at least 2 to 5 hours. Once a substantially homogenous liquid is formed the mixture may be transferred to moulds and allowed to set.

In a preferred form of the invention the composition is allowed to mix for at least about 6, 7, 8, 9, 10, 11, 12, 13, 14, 15, 16, 17, 18, 19, 20, 21, 22, 23, 24, 25 hours. In the exemplified method, the composition was allowed to mix for at least 16 hours.

In an alternate form of the invention the active ingredient (for example flucloxicillin) may react with one or more of the additives (eg PEG) in the composition or product. In those circumstances stirring is preferably restricted to within 2 h to fabricate tablets that have drug content above 90% of label claim.

In a specific form of the above invention the method includes the steps of:
a. mixing at least the active ingredient, the masking agent and or the firming ingredient to produce a homogenous mixture
b. combining the mixture of step (a) with a surfactant
c. combining the mixture of step (b) with the chocolate of chocolate substitute wherein step (c) is performed for at least 4 hours to ensure that a substantially homogenous product is produced.

Where the composition or product includes additional additives, those additives are preferably added to the com- position during step (a).

Each of the mixing steps of the invention can be con- ducted in the presence of heat to ensure that a homogeneous blend of the product is achieved at each step of the method. Preferably step a is performed with heat from about 35 to 60 degrees Celsius. Ideally it will be around 55 degrees Celsius.

In a highly specific example, the method includes the steps of
a. Mixing midazolam hydrochloride, Cremophor RH40, sodium chloride, steviol glycoside and xanthan gum using a stirrer hot plate set at about 55° C. until homogeneously dispersed;
b. Combining polyethylene glycol to the mixture of step (a) and mix;
c. Combining the chocolate base to the mixture, stir to melt and mix until fully incorporated;

wherein the mixture of step (c) is then mixed for a further 16 hrs to produce a homogeneous product.

The homogeneous composition produced from the method may be moulded into any shaped product as desired.

According to a sixth embodiment of the invention there is provided a method of delivering to a compound to a subject, said method comprising the steps of: (a) preparing a product as described herein; and (b) administering a therapeutically effective amount of the product to the subject.

In a preferred form of this embodiment and other embodiments of the invention, the therapeutic dose will be less than 500 mg, more preferably less than 400, 300, 200, or 100 mg. One skilled in the art will understand that the dose of compound to be delivered will depend on the amount to chocolate or chocolate substitute that a subject ingests. In a preferred illustrative form, the dose will be 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 49, 40, 41, 42, 43, 44, 45, 46, 47, 48, 49, 50, 51, 52, 53, 54, 55, 56, 57, 58, 59 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg. For example, Clindamycin HCl was incorporated at 40.7 mg per tablet (1 g mould), but the tablet is 2× the size of the midazolam tablet (500 mg mould).

According to a seventh embodiment of the invention, there is provided a method of treating a subject with an ailment or a condition, said method comprising the steps of: administering to the subject a therapeutically effective amount of, (i) a chocolate or chocolate substitute composition or product as describe herein, or a (ii) chocolate or chocolate substitute composition or product produced by a method of the invention.

According to an eighth embodiment, the invention resides in the form of a chocolate or chocolate substitute liquid or beverage prepared by fluidizing the chocolate or chocolate substitute composition or product of the invention described herein.

Further features of the present invention are more fully described in the following Examples. It is to be understood, however, that this detailed description is included solely for the purposes of exemplifying the present invention, and should not be understood in any way as a restriction on the broad description of the invention as set out above.

EXAMPLES

Example 1

Development of Solid Chocolate Formulations of Midazolam that are Palatable, Safe, Effective, and of Good Quality Applying iterative development and optimization techniques, and the art of chocolate manufacture, the inventors have successfully formulated prototype chocolate mini tablets containing 5 mg of midazolam hydrochloride using chocolates (Nestlé or Valrhona) and approved food and pharmaceutical excipients (steviol glycosides, sodium chloride, polyethylene glycol, Cremophor, and xanthum gum). In particular the inventors developed a midazolam hydrochloride chocolate tablet of stable form having the following composition:

| Quantity per unit | Starting material |
|---|---|
| 5 mg | Midazolam Hydrochloride |
| 1 mg | Sodium chloride, finely ground |
| 2 mg | Steviol glycoside |
| 5 mg | Xanthan gum |
| 50 mg | Cremophor RH40 |
| 100 mg | Polyethylene glycol 1450 |
| 404 mg | Dark chocolate base |

More specifically the tablets had the following composition:

| Ingredient | Weight used for 10 tablets (mg) | Weight per tablet (mg) | Percent weight in each tablet | Dose (mg/kg/day) based on a midazolam dose of 0.5 mg/kg/day in paediatrics |
|---|---|---|---|---|
| Dark chocolate | 4026.7 | 403 | 71.33 | 40.3 |
| Midazolam HCl | 50 | 5 | 0.88 | 0.5 |
| NaCl | 10 | 1 | 0.18 | 0.1 |
| Steviol | 10 | 1 | 0.18 | 0.1 |
| Xanthum gum | 50 | 5 | 0.88 | 0.5 |
| Cremophor RH40 | 500 | 50 | 8.85 | 5 |
| PEG 1450 | 1000 | 100 | 17.70 | 10 |

The above ingredients were mixed in the following procedure, having the following steps:
a. Each of the following ingredients was measured midazolam hydrochloride, Cremophor RH40, sodium chloride, steviol glycoside and xanthan gum then placed into a porcelain evaporating basin.
b. Using a magnetic stirrer hot plate set at 55° C. and a propylene stirring rod, manually the ingredients were mixed until homogeneously dispersed.
c. Polyethylene glycol was then added to the mixture, and the mixture was stirred to melt and mix.
d. The Chocolate base was added to the mixture, and was stirred until fully incorporated, heat was applied as necessary to melt the mix.
e. The mixture was then transferred to a PTFE stirrer bar and was allowed to mix using a magnetic stirrer set to 200 rpm.
f. The mixture was allowed to mix overnight (16 h).
g. The mixture was then transferred to the ½ g troche moulds using a sterile disposable syringe, carefully filling each mould and ensuring there is no air pocket.
h. The tablets were left to set for a few hours or overnight at room temperature, loosely covered with foil.
i. The tablets were removed from the moulds.
j. Each tablet was then weighed to check for uniformity in weight.
k. Each tablet (or part) was wrapped in a piece of lightweight foil and stored at ambient temperatures away from heat.

Taste evaluation by the PIs suggests that the chocolate formulation was effective in masking the bitter taste of midazolam and offers a definitive superior alternative to the midazolam syrup currently available for paediatric patients.

Preliminary analysis using a high performance liquid chromatographic assay developed in our laboratory further confirmed the midazolam content (99.47±0.61% of label strength, n=6) and the absence of apparent degradation materials in the chocolates. This suggests the drug had remained intact throughout the mild production process. The tablet production was validated for scaled up manufacture to produce clinical samples for taste perception, pharmacokinetic and pharmacodynamic studies, following tablet quality and stability assessments.

Drug Content and Content Uniformity
Methods

Three tablets were analysed each time at ambient temperature. Each tablet was weighed into 100 mL volumetric flasks followed by addition of 25 mL methanol and 15 mL deionized water. The flasks were then heated on a water bath with gentle manual agitation till the chocolate was completely dispersed into solution. Another 50 mL of methanol was added to each flask and the mixture was sonicated in a water bath (Ultrasonic Cleaner FXP 8D, Unisonics Australia, NSW, Australia) for 4 min to further dissolve the chocolate. The solution was then cooled to room temperature, made up to 100 mL with methanol, and filtered (0.2 μm) for HPLC analysis. The drug content was expressed as a percentage of label claim, which was 5 mg midazolam hydrochloride (HCl) per tablet.

Midazolam quantifications were performed by reversed phase HPLC. Drug content in the chocolate tablets was quantified on a Hewlett Packard Series 1100 HPLC equipment using a C18 column (Gemini NX, 5 μm, 150×4.6 mm) (Phenomenex, Lane Cove, NSW, Australia). An isocratic elution at a flow rate of 1 mL/min was employed, with midazolam detected at 250 nm. The mobile phase consisted of 36% v/v acetonitrile and 64% v/v potassium phosphate buffer (20 mM phosphate, pH 3.8). An autosampler was used with the HPLC, and all midazolam samples for HPLC analysis were stored in amber HPLC glass vials to minimise light-induced degradation of midazolam in the samples. The HPLC was calibrated with standard solutions prepared by dissolving midazolam HCl at 1, 2, 5, 7, 10 and 50 μg/mL in methanol.

Results

HPLC assay data indicated that the mean drug content on day 0 in the chocolate tablets (n=27) was 102.53±3.00% of the stated midazolam HCl content (5 mg). This, together with the absence of apparent degradation materials in the chromatogram, suggests that the drug had remained intact throughout the mild production process. Drug content uniformity was also verified using the US pharmacopoeia specification for drug content uniformity for tablets with less than 25 mg of active drug per tablet. Acceptance of drug content uniformity was determined by calculating the mean value and the acceptance value for the drug content of 10 tablets. If the acceptance value is 15, the drug content is acceptable. Ten midazolam chocolate tablets were analysed to have a mean drug content of 100.46% and an acceptance value of 5.76, suggesting an acceptable drug content uniformity.

Stability Data

Methods

The midazolam chocolate tablets immediately after manufacture were individually wrapped in aluminum foil and stored in amber glass bottles at ambient temperature. At specified time intervals, triplicate tablets were removed for analysis of gross morphology, following which they were analysed for midazolam HCl content.

The midazolam HCl content was assayed using an Agilent HPLC system (Agilent 1260 Infinity HPLC, Agilent Technologies Australia, Mulgrave, NSW, Australia) equipped with an automatic sampler, degasser, binary pump and MWD detector. Data from detector were collected and analysed with the Open Lab software. HPLC separations were carried out on a ODS Hypersil C18 (100×4.6 mm, 5 μm) column (ThermoFisher Scientific, Malaga, WA, Australia) protected with a BDS-Hypersil-C18 Guard column (10×4 mm, 3 μm) (ThermoFisher Scientific, Malaga, WA, Australia). An isocratic method was used for separation of the analytes. The mobile phase consisted of acetonitrile and 0.1% (v/v) triethylamine (45:55, v/v). The 0.1% triethylamine was filtered through a 0.45 μm nitrocellulose filter membrane (MERCK Millipore, Bayswater, VIC, Australia) before use. The flow rate was 0.6 mL/min, at ambient temperature, and absorbance of the eluent was monitored at 250 nm. The injection volume was set to 20 μL. The HPLC was calibrated with standard solutions prepared by dissolving midazolam HCl at 1, 2, 5, 7, 10 and 50 μg/mL in methanol.

Results

The midazolam HCl content in the chocolate tablets was found to remain above 90% of label claim for at least 18 months storage at ambient temperatures (FIG. 1). The physical appearance of the tablets was also not affected by storage for at least 18 months at ambient temperature. These data suggest that the midazolam chocolate tablets are stable for at least 18 months when stored at ambient temperature, and they do not require cold chain transport and storage.

In Vitro Drug Dissolution Profile

Methods

In vitro drug dissolution tests for the midazolam chocolate tablets was carried out using a method adapted from the British Pharmacopoeia (BP, 2013) dissolution methods described for nitrazepam, oxazepam and temazepam tablets as the BP did not have a monograph for midazolam HCl tablets.

The drug dissolution test was conducted using the USP Apparatus 2 with the paddle rotating at 50 revolutions per minute (Varian VK 7010 Dissolution Apparatus, Agilent Technologies, Mulgrave, Victoria, Australia). The dissolution fluid was 500 mL of 0.1M hydrochloric acid at 37° C., the volume being lower than the 900 mL typically employed for BP-specified dissolution experiments. The reason for this was that all dissolution samples withdrawn for HPLC analysis had to be diluted 1:1 with 100 mM phosphate buffer (pH 4.2) as the dissolution medium was too acidic for direct injection into the HPLC. In order that the dilution did not affect the sensitivity of the HPLC assay, a near 2-fold reduction in the volume of medium was used for the dissolution experiments. The pH 4.2 phosphate buffer was chosen as the diluent because the imidazole ring in the midazolam molecule undergoes ring opening at pH below 4, giving rise to the open-ring benzophenone structure. Under the HPLC conditions employed in this project, the HPLC peak attributable to the benzophenone structure was observed at a retention time of 2.1 min, compared with 6.3 min for the molecular midazolam. The former could not be completely resolved from the solvent peaks, making quantification difficult. Transformation of the benzophenone structure is reversible, and the open-ring structure can be readily and completely converted to the molecular midazolam by adjusting the medium pH to ≥4. However, midazolam has a $pK_a$ of 6.57, and its solubility in aqueous media is adversely affected at pH between 4.2 and 4.97. The very narrow pH window afforded by the opposing phenomena led us to dilute the dissolution samples with the pH 4.2 phosphate buffer. This brought the dissolution sample pH from <2 to 4.2, which was found satisfactory in ensuring that only the molecular midazolam existed in the samples when they were injected into the HPLC for analysis.

To initiate the dissolution test, the chocolate tablet was weighed into a 15-mL porcelain crucible. To simulate the chewing of the tablet by the patient, the tablets were crushed roughly in the crucible using a glass rod, and the weight of the crushed tablet was recorded. The crucible was then lowered with the help of forceps into the dissolution vessel containing 500 mL of 0.1 M hydrochloric acid at 37° C. The crucible was shaken vigorously to dislodge and disperse the tablet fragments in the dissolution medium, thus simulating the mixing of the chocolate tablet with saliva in the oral cavity of patients. The crucible was left at the bottom of the vessel, out of the way of the rotating paddle. Aliquots of 1 mL were sampled from the dissolution medium every 15 min, starting immediately upon placement of the crucible in the dissolution medium (0 min) and taking the last sample at 60 min. The withdrawn aliquot was immediately replaced by adding 1 mL of fresh dissolution medium into the vessel after each sampling.

For HPLC analysis, 0.5 mL of a 100 mM phosphate buffer was added into an amber HPLC vial containing 0.5 mL of the filtered dissolution sample (Fitropur S 0.2 μm filter, Sarstedt Australia Pty. Ltd, Adelaide, SA, Australia). The diluted dissolution sample was then analysed in triplicates using the HPLC assay described in section (1). The cumulative amount of drug released, expressed as a percent of the initial drug load (5 mg) in the tablet, was plotted against the sampling time to give the in vitro drug dissolution profile. The HPLC was calibrated with standard solutions prepared by dissolving midazolam HCl at 1, 2, 3, 4, 5 and 10 μg/mL in a solvent comprising 1:1 v/v of 0.1 M hydrochloric acid and 100 mM phosphate buffer (pH 4.2). Dissolution experiments were conducted for triplicate tablets on the day of manufacture and after 28 days of storage at ambient temperatures.

Results

Figure 2:
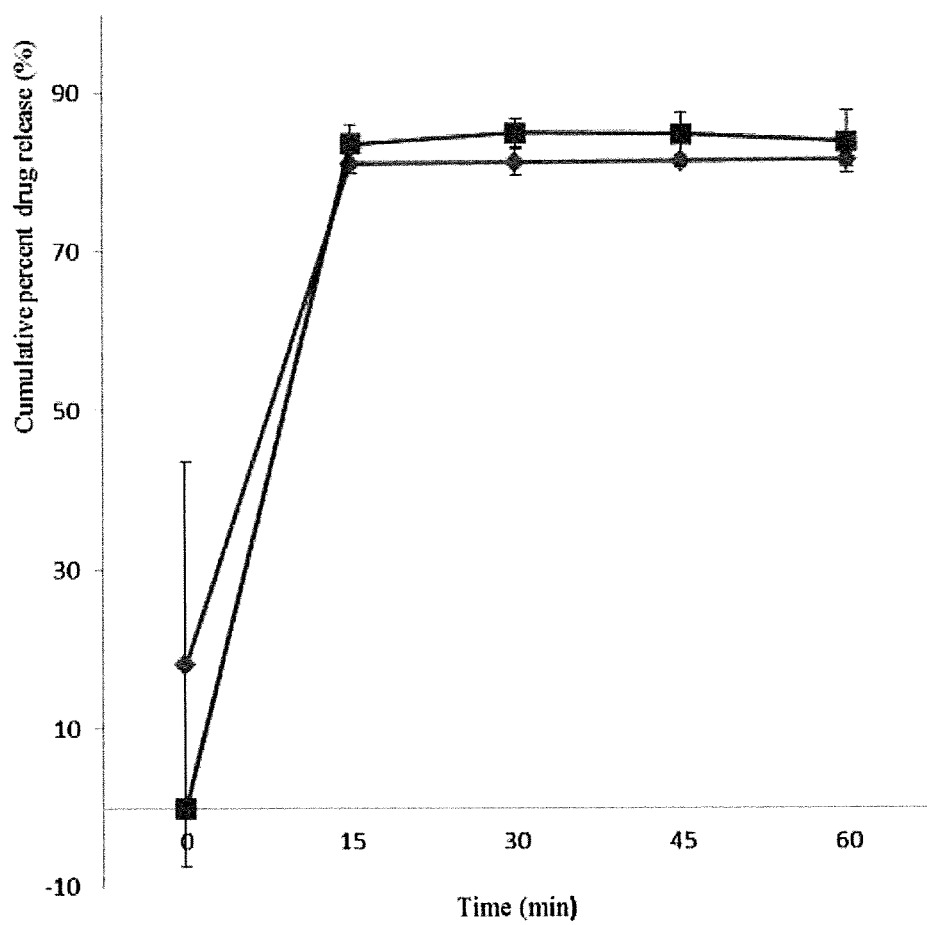
FIG. 2 presents In vitro drug dissolution profiles of midazolam chocolate tablets on the day of manufacture (blue line) and after storage at ambient temperature for 28 days (red line).

For immediate release oral solid dosage forms, the typical BP specification is for at least 80% of the drug load to be released within 15-30 min in the dissolution medium. Tablets analysed on the day of manufacture met this requirement, the dissolution profile showing a release of 81.37±0.85% (n=3) of the midazolam HCl load after 15 min in the dissolution medium (FIG. 2). No significant increase in cumulative drug release was observed between 15 and 60 min. A comparable drug dissolution profile was obtained after the tablets had been stored for 28 days at ambient temperatures, the cumulative amount of drug released at 15 min being 84.79±2.76% (FIG. 2).

Parallel In Vitro Drug Dissolution Profile

In vitro drug dissolution tests were conducted using the USP Apparatus 2 with the paddle rotating at 50 rpm (Varian VK 7010 Dissolution Apparatus, Agilent Technologies, Mulgrave, Victoria, Australia). To initiate the dissolution test, triplicate midazolam tablets were individually weighed into separate porcelain crucibles, and the chewing of the tablets was simulated by crushing each pliable tablet with a glass rod. The crushed tablets were reweighed to confirm negligible material loss before placing into 500 mL of 0.1 M HCl at 37° C. The tablet fragments were dislodged and dispersed into the medium to simulate the mixing of the chocolate tablet with saliva in the oral cavity of patients. Aliquots of 1 mL were sampled from the dissolution medium at 0, 5, 15, 30, 45 and 60 min, and the withdrawn aliquot was immediately replaced with 1 mL of blank dissolution medium. The aliquot samples after filtration (Fitropur S 0.2 μm filter, Sarstedt Australia Pty. Ltd, Adelaide, SA, Australia) were mixed 1:1 v/v with methanol and analysed by a validated high performance liquid chromatographic (HPLC) assay. The cumulative amount of drug released was expressed as a percent of the initial drug load in the tablet, and plotted against sampling time to provide the in vitro drug dissolution profile. Parallel experiments were performed using whole tablets in the same dissolution medium, and using crushed tablets with 300 ml of simulated saliva (8 mg/ml sodium chloride, 0.19 mg/ml potassium phosphate monobasic, 2.38 mg/ml sodium phosphate dibasic, pH 6.8) (18) as the dissolution vehicle. Aliquots withdrawn from the simulated saliva dissolution medium were diluted 1:1 v/v with blank simulated saliva medium for the HPLC assay.

Midazolam HCl was quantified by reversed-phase HPLC (Agilent 1260 Infinity binary pump HPLC, Agilent Technologies Australia, Mulgrave, NSW, Australia) with a Sunfire C18 column (3.5 μm, 100×3.0 mm) (Waters Australia Pty Ltd, Rydalmere, NSW, Australia). A gradient elution at flow rate of 0.45 mL/min was employed where the mobile phase of 25% v/v acetonitrile (ACN) and 75% v/v potassium phosphate buffer (20 mM phosphate, pH 3.8) was graded to 100% ACN in 6 min, then held isocratic for the next 6 min. Midazolam was detected at 237 nm. Linearity of calibration graphs ($R^2 > 0.99$) were demonstrated over the concentration ranges of 0.04 to 25 μg/ml, and 0.5 to 20 μg/ml for the standard solutions of midazolam HCl in 0.1 M HCl and simulated saliva (pH 6.8), respectively. To overcome the poor aqueous solubility of midazolam HCl at pH 6.8, the drug was initially dissolved at 200 μg/ml in simulated saliva adjusted to pH 3.1 with HCl. This stock solution was then diluted with simulated saliva, pH 6.8, to the required final concentrations. Standard solutions in 0.1 HCl were diluted 1:1 v/v with methanol, while those in simulated saliva were diluted 1:1 with blank simulated saliva prior to assay in the HPLC.

Results

Figure 3:
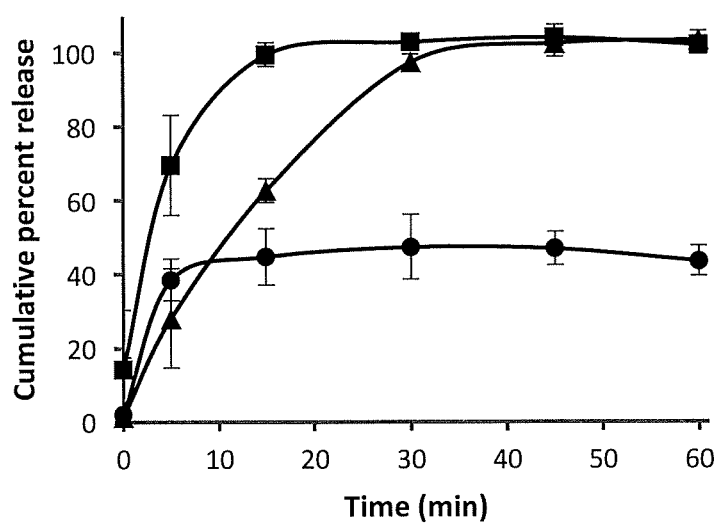
FIG. 3 In vitro drug release profile from the midazolam chocolate tablet into simulated dissolution media at 37° C.; (a) ▲—whole tablet in 0.1 M HCl; (b) ■—masticated tablet in 0.1 M HCl; and (c) ●—masticated tablet in simulated saliva, pH 6.8. Data represent mean±SD, n=3.

There was complete release (99.52±3.22%, n=3) of the midazolam HCl load from the masticated tablets after 15 min in the 0.1 M HCl medium (FIG. 3). At the zero time point, the mean amount of drug already available from these tablets was 0.62±0.70 mg, equivalent to 14.26±16.18% of the drug load in the tablets. If the tablets had not been crushed prior to exposure to the dissolution medium, the mean cumulative drug released at t=0 and t=15 min were 1.25±0.47% and 62.78±4.87%, respectively. The full drug load (~100%) was released from the intact tablets at about 35 min (FIG. 3). Changing the dissolution medium for the crushed tablets from 0.1 M HCl to simulated saliva (pH 6.8) significantly inhibited the amount of drug released from the tablets. The cumulative percent drug released reached a plateau value of about 45% at 10 min, and this level was maintained over the next 50 minutes, i.e. the duration of the experiment (FIG. 3).

Other Methods of Administration of the Midazolam Chocolate Tablets

Methods

To evaluate whether the midazolam chocolate tablets could be administered as a liquid, three tablets were separately weighed into 15 mL crucibles with 2 mL boiling water added to each tablet. Following complete dissolution with manual stirring, the liquid chocolate mixtures were left at ambient temperature for 1 h. The drug content was then analysed by transferring the mixtures into 100 mL-volumetric flasks and extracting the drug into 80 mL of methanol and 13 mL of hot water. After the mixtures had cooled to room temperature, methanol was added to make up to volume. The solutions were syringe filtered and the drug content analysed by a HPLC assay as described in section [0102].

A liquid formulation was also prepared. Instead of casting the liquid midazolam chocolate pre-mix into the troche moulds to form tablets, a weighed quantity of the pre-mix containing 250 mg of midazolam HCl, together with 1 mL of a preservative solution containing 8% (w/v) methyl hydroxybenzoate and 2% (w/v) propyl hydroxybenzoate in propylene glycol, was mixed with an adequate amount of water to yield 100 mL of solution. The final liquid midazolam chocolate formulation contained 2.5 mg/mL midazolam HCl, which was deemed appropriate for use in the paediatric population. Two batches of the liquid formulation were prepared and, immediately after preparation, each batch was aliquoted into four 20 mL-amber glass bottles. Two bottles were stored at room temperature (21-23° C.) and the other two were stored refrigerated at 4-8° C. At specified time points, the samples were evaluated for gross appearance and ease of dispersion. To test for drug content, 1 mL aliquot of the liquid formulation was weighed into a 50 mL volumetric flask, and heated with 20 mL of a 5:3 (v/v) methanol:water solution over a water bath with manual agitation. Twenty-five mL of methanol was then added followed by sonication over 4 min, and the solution was allowed to cool before it was made up to volume with methanol. Approximately 2 mL of each solution was syringe-filtered into separate amber glass HPLC vials and analysed for drug content using the validated HPLC assay method described in section [0102].

Results

Reconstituting the midazolam chocolate tablets with hot water did not cause the drug to degrade, the residual midazolam HCl content in the reconstituted liquid after 1 hour at ambient temperature was 103.80±0.06% (n=3) of the label claim.

Figure 4:
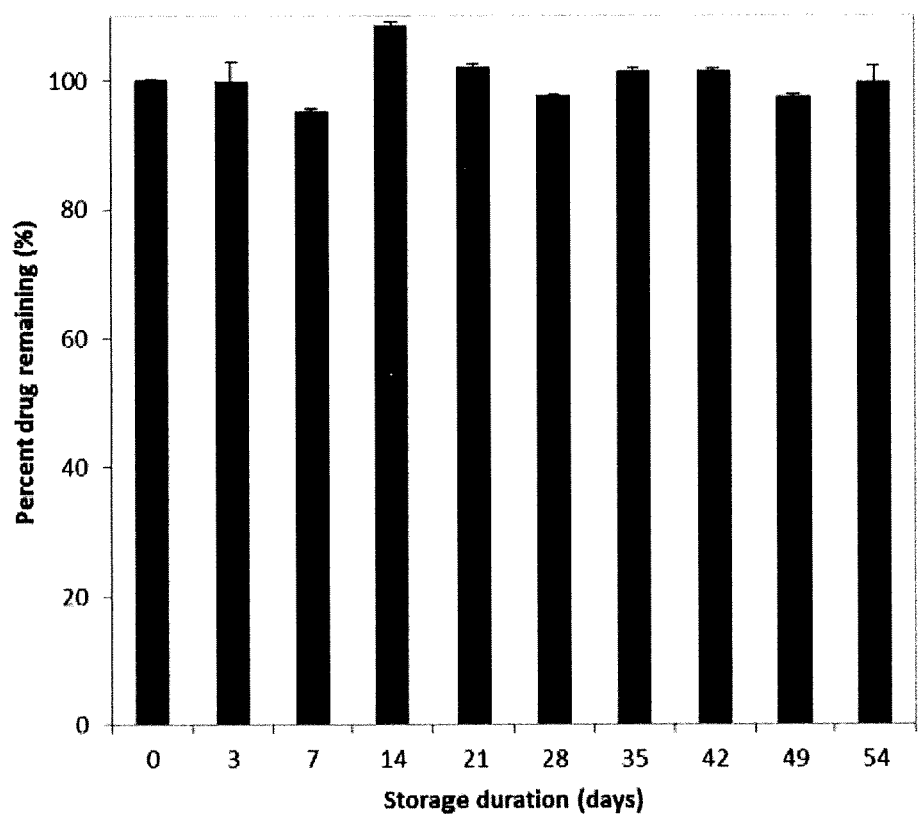
FIG. 4 illustrates Percent drug remaining in oral liquid (2.5 mg/mL) reconstituted by dissolving the midazolam chocolate tablets in water and stored at refrigerated temperature. Data represents mean±SD (n=3).

The oral midazolam chocolate liquid formulation (2.5 mg/mL of midazolam HCl) prepared by mixing the pre-mix with preserved water was a homogeneous liquid with the thick, uniform consistency and appealing odour typical of melted chocolate. These physical attributes were maintained for up to 3 days storage at both room and refrigerated temperatures. At day 7, the liquid formulation stored at ambient temperatures had developed a foul smell indicative of microbial contamination, and white spots together with an increase in viscosity were noted. Drug content was not determined because aliquots could not be accurately withdrawn from these samples. In contrast, the 3 liquid samples stored at refrigerated temperature retained their physical attributes and at least 90% of their drug content for at least 56 days post-manufacture (FIG. 4). This suggests that, for children who must have a liquid midazolam medication, the midazolam chocolate tablets can be rendered into a liquid preparation that is stable when stored at refrigerated temperature for at least 56 days.

Taste Evaluation in Animal Model

Method

All animal procedures were carried out in accordance with the UK Animals (Scientific Procedures) Act 1986 (Project Licence PPL 70/7668).

The rat 'Brief-Access Taste Aversion' (BATA) model was used to assess the taste of the midazolam chocolate tablet formulation relative to control samples. Ten male Sprague Dawley rats (average weight 745 g) previously trained for the experiments were used and two independent tasting evaluations were conducted over 2 days.

Prior to the experiments, the rats were water-deprived for 22 hours but had access to food ad libitum. Each rat was placed into the Lickometer Davis Rig MS-160 (DiLog Instruments, Tallahassee, Fla., USA) for a 40-minute session where it would be presented with 16 sipper tubes mounted on a moving rack controlled by the Davis Collect Data software. The taste samples were each presented to the rat for 8 seconds, in a random order specified by the computer program. Over the 40-minute session, a sample would have been presented to the rat four times, with a 2-second water rinse given between samples. As the rats licked on the sipper, the number of licks was recorded electronically and transmitted to a database on a computer.

The 5 mg midazolam HCl chocolate tablets were assessed against control samples, which included deionized water, vehicle (water adjusted to pH 5 with HCl), 1 mg/mL solution of midazolam in the vehicle, a 2.5 mg/mL oral midazolam syrup manufactured by AUSPMAN, and chocolate placebo tablets. Simulating the advice to patients to chew the chocolate tablet and then swallow, the placebo and midazolam-loaded chocolate tablets were prepared for the taste evaluation by grinding each chocolate tablet in 2 mL of water, which mimics the volume of saliva, using a mortar and pestle. The resultant liquid preparations were then presented to the rats. Calibration of midazolam taste threshold was also performed by including within each 40-min session standard solutions prepared by dissolving midazolam HCl in the vehicle at concentrations ranging from 0.003 to 1 mg/mL.

Aversion to the taste of a sample was indicated by a significant reduction in the number of licks when the sample was presented to the rats. While all attempts were made to conduct the experiments in a room devoid of distractions, the rats were sometimes distracted and a waiting time to first lick of 20 seconds was imposed. In addition, where a sample attracted 0 or only 1 lick, this was discounted as outliers for the final analysis of data. Data was analysed using the RStudio software (https://www.rstudio.com) and applying the non-parametric Kruskal Wallis test with post-hoc Tukey's test for paired comparisons.

Results

Figure 5A:
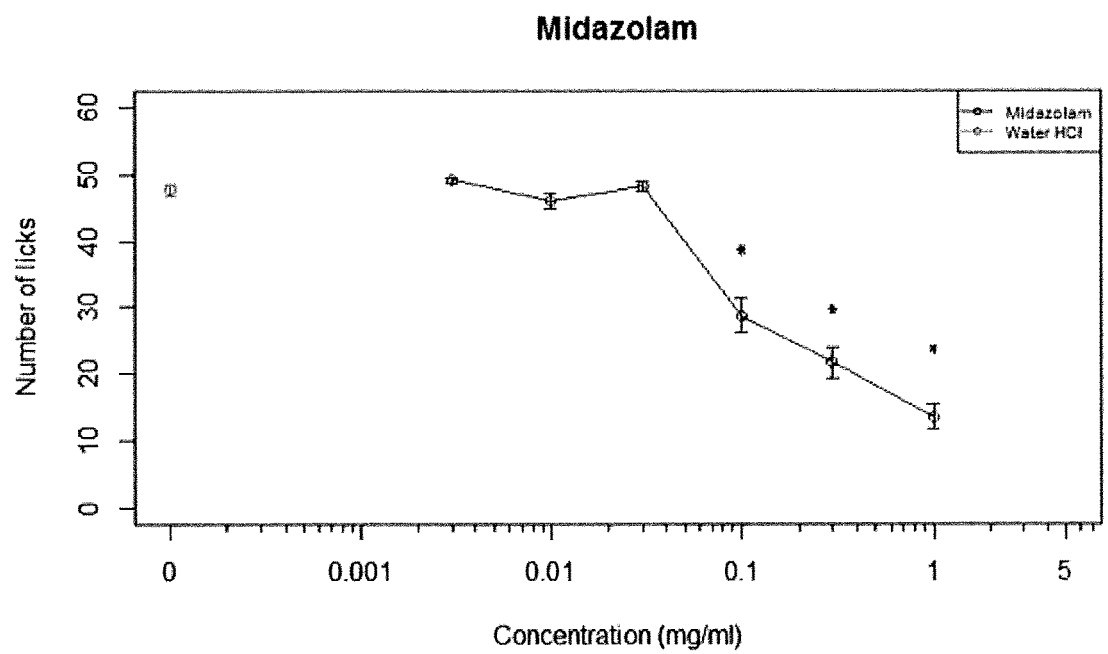
FIG. 5 illustrates Response of Sprague Dawley rats (n=10, data represent the sum of 2 independent experiments conducted over 2 days, mean±SE) to the taste of different midazolam samples (A) midazolam standard solutions prepared by dissolving midazolam HCl in the vehicle; and (B) test samples comprising deionized water; vehicle; dark chocolate placebo (500 mg dissolved in 2 mL of water); standard 1 mg/mL midazolam HCl solution in vehicle; 2.5 mg/mL oral syrup manufactured by AUSPMAN; and 5 mg midazolam HCl chocolate tablet dissolved in 2 mL of water to give a chocolate liquid containing 2.5 mg/mL midazolam.

Solutions containing up to 0.03 mg/mL midazolam HCl received comparable numbers of licks from the rats compared to the blank vehicle (FIG. 5A), suggesting that the rats were unable to effectively detect the bitter taste of the drug presented at very low concentrations. However, there was a significant drop in the number of licks when the drug concentration was increased to 0.1 mg/mL, with further decreases in the number of licks noted as the drug concentration was increased to 0.3 and 1.0 mg/mL. The dose-response curve obtained from the midazolam HCl standard solutions suggest a mean IC50 value of 0.30±0.29 mg/mL (n=2) (FIG. 5A).

Figure 5B:
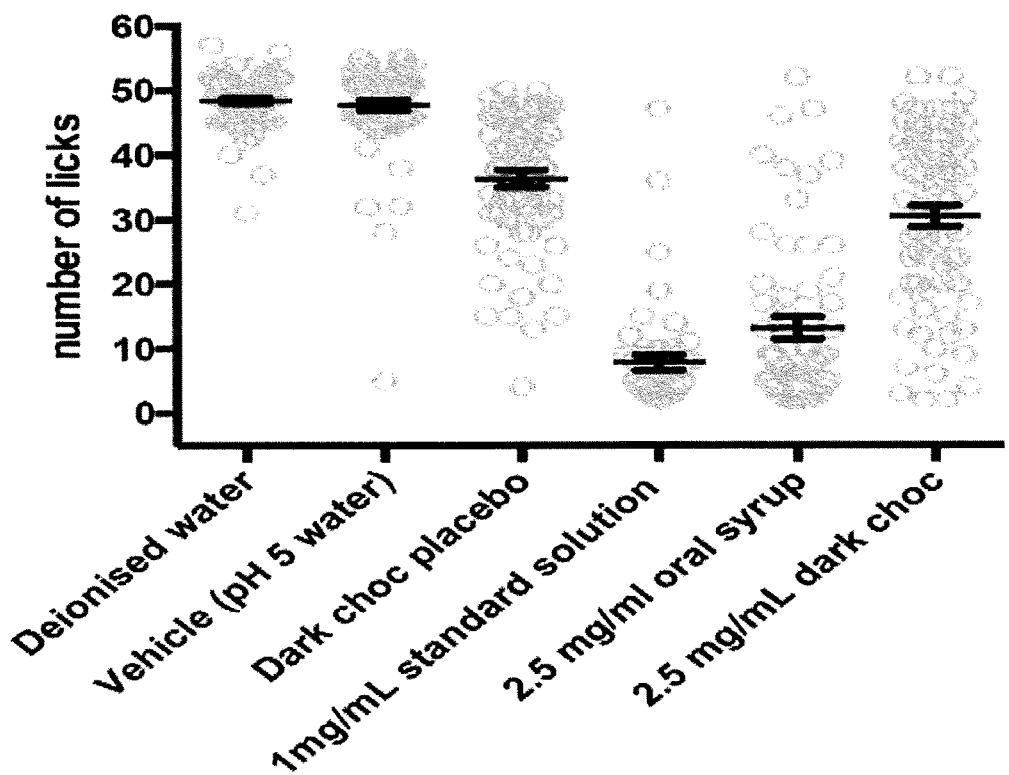

FIG. 5B shows that, compared to the standard 1 mg/mL midazolam HCl solution (vehicle=water at pH 5), the liquid midazolam chocolate sample prepared by dissolving the 5 mg midazolam chocolate tablet in 2 mL of water was significantly better received by the rats. This is despite the chocolate sample having a 2.5 fold higher midazolam HCl content than the standard solution. The mean number of licks for the midazolam chocolate sample was comparable to that for the placebo chocolate tablet, suggesting that the rats were unable to detect the bitter midazolam when it was presented in the chocolate sample. In contrast, the oral syrup prepared by AUSPMAN, which also contained 2.5 mg/mL midazolam HCl, was less well received, in spite of the employment of sweetening agents and flavouring agents, including a chocolate flavour in the syrup formulation.

Taste Evaluation in Paediatric Patients

Method

This is a prospective, open-label, single centre, randomised, single treatment trial implemented at the Princess Margaret Hospital for Children. For ethical reasons, the study involved only paediatric patients undergoing elective surgery who have been prescribed midazolam for pre-medication prior to the induction of anaesthesia by an anaesthetist independent of the study team at the Princess Margaret Hospital. The study planned to recruit 150 children (75 for chocolate test sample, 75 for comparator midazolam sample) aged 3-16 years of age, and was approved by the Princess Margaret Hospital Human Research Ethics Committee (HREC reference number: 2014102EP).

All participants were recruited on the day of their procedure. Once confirmed midazolam was required for premedication prior to the induction of anaesthesia by the treating anaesthetist, patients were contacted by an experienced research nurse/research assistant and informed about voluntary participation in this study. Both gender aged 3-16 years who have been prescribed midazolam as a pre-medication by the treating anaesthetist, independent of the study team, were included in the study. Children who are allergic to midazolam and/or chocolate were excluded.

Written informed parental consent as well as child assent were sought prior to inclusion into the study protocol. Each child was randomised by computer generated block randomization, stratified by gender and age (<7 years old, ≥7 years old), to receive by mouth either the chocolate-based midazolam tablet, or an IV midazolam solution, which is the current mode of midazolam administration at the hospital. Participants assigned to the chocolate tablet were instructed to chew the tablet before swallowing. Midazolam as a pre-procedural medicine was to be dosed at 0.5 mg/kg according to local institutional guidelines. However, the doses administered to the participants in this study were determined by the treating anaesthetist, and they ranged from 0.16 to 0.55 mg/kg.

Figure 6:
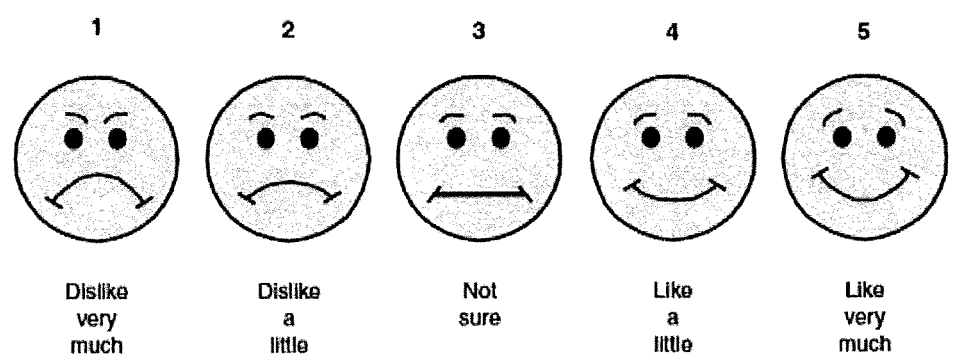
FIG. 6—The five-point facial hedonic scale.

After ascertaining the patient has taken the allocated midazolam sample, a trained interviewer would record whether the whole dose was swallowed or the tablet was partially spat out or totally refused. She would also record on a five-point facial hedonic scale (FIG. 6) whether the child liked the taste of the medication. The child was also asked to record how much he/she liked the sample by putting a mark on a separate five-point facial hedonic scale, and whether he/she would be happy to take the sample again if unwell. The attending caregiver was also asked to give a score on another five-point hedonic scale on how he/she perceived the child's response to the taste of the assigned medication. If the child had spat out the dose immediately after administration, the treating anaesthetist would decide, in line with current hospital management protocol, whether a second midazolam dose was required. If the second dose was recommended, the treating anaesthetist along with the parent/child would decide on whether the same allocated midazolam sample or the alternative midazolam sample should be administered. All assessments were recorded in the Patient Assessment Form.

Results

A total of 150 children were included in the taste analysis study, with 76 in the IV solution group and 74 in the midazolam chocolate tablet group (Table 1). There were no significant demographic differences between the two groups.

Of the 150 children, 20 did not entirely ingest the first dose (12 in IV group, 6 in chocolate group, p>0.05), and 2 in the IV group entirely refused the dose. For 3 children who refused the IV dose, the midazolam chocolate tablet was given as a second dose. Two of the three entirely ingested the chocolate tablet, while the third partially ingested this dose.

|  | IV formulation | Chocolate formulation | P value |
|---|---|---|---|
| Number | 76 | 74 |  |
| Weight (kg) | 23 [19-32] | 24 [19-35] | 0.79 |
| Age (years) | 6.6 [4.4-9.1] | 6.8 [4.9-9.6] | 0.86 |
| Male | 37 (49) | 36 (49) | 0.87 |
| Height (cm) | 119 [109-133][a] | 120 [111-136][a] | 0.66 |

[a]Height missing for one participant in each group.

TABLE 1

Baseline characteristics for 150 children administered midazolam orally via an IV formulation or chocolate tablet formulation. Data presented as number (percentage) or median [interquartile range].

|  | Score by participants (mean ± SD) | Score by parents (mean ± SD) | Score by nurses (mean ± SD) |
|---|---|---|---|
| IV Solution Group (n = 76) | 1.71 ± 1.13 [a] | 1.71 ± 1.00 | 1.97 ± 1.00 |
| Chocolate Group (n = 74) | 3.16 ± 1.45 [a] | 3.52 ± 1.25 | 3.36 ± 1.29 |
| P value | <0.0001 | <0.0001 | <0.0001 |

[a] no score from 4 children in IV group and 1 child in chocolate group

Table 2 Summary of acceptability scores given by participants and attending parents and nurses for midazolam IV solution and midazolam chocolate tablet administered orally. Scores ranged from 1 to 5, with 5 being 'like very much'.

Figure 7:
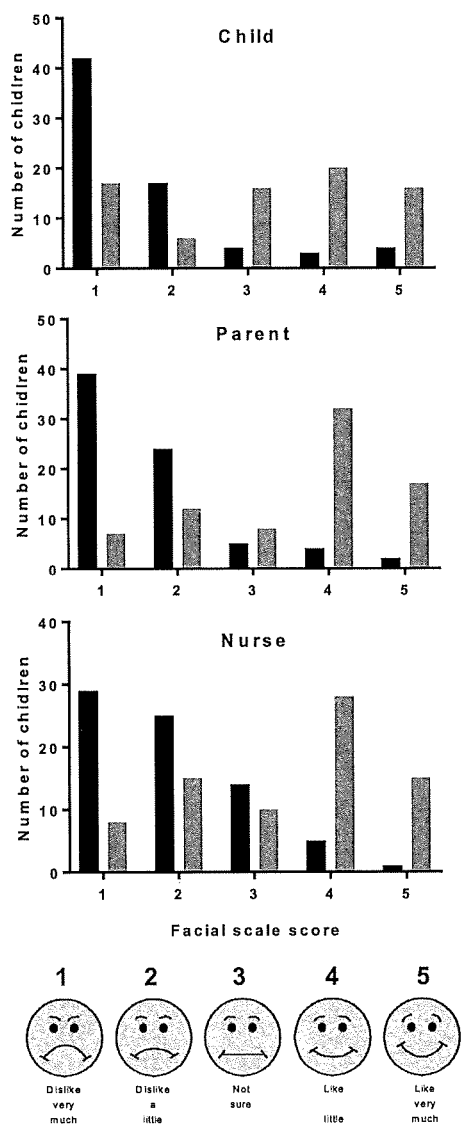
FIG. 7—Histogram of scores given by child patient, parent and nurse indicating acceptability for the midazolam IV solution formulation (black bars) and novel midazolam chocolate tablet formulation (grey bars). A 5-point facial hedonic scale was used for assessment of taste of the formulations.
Figure 8:
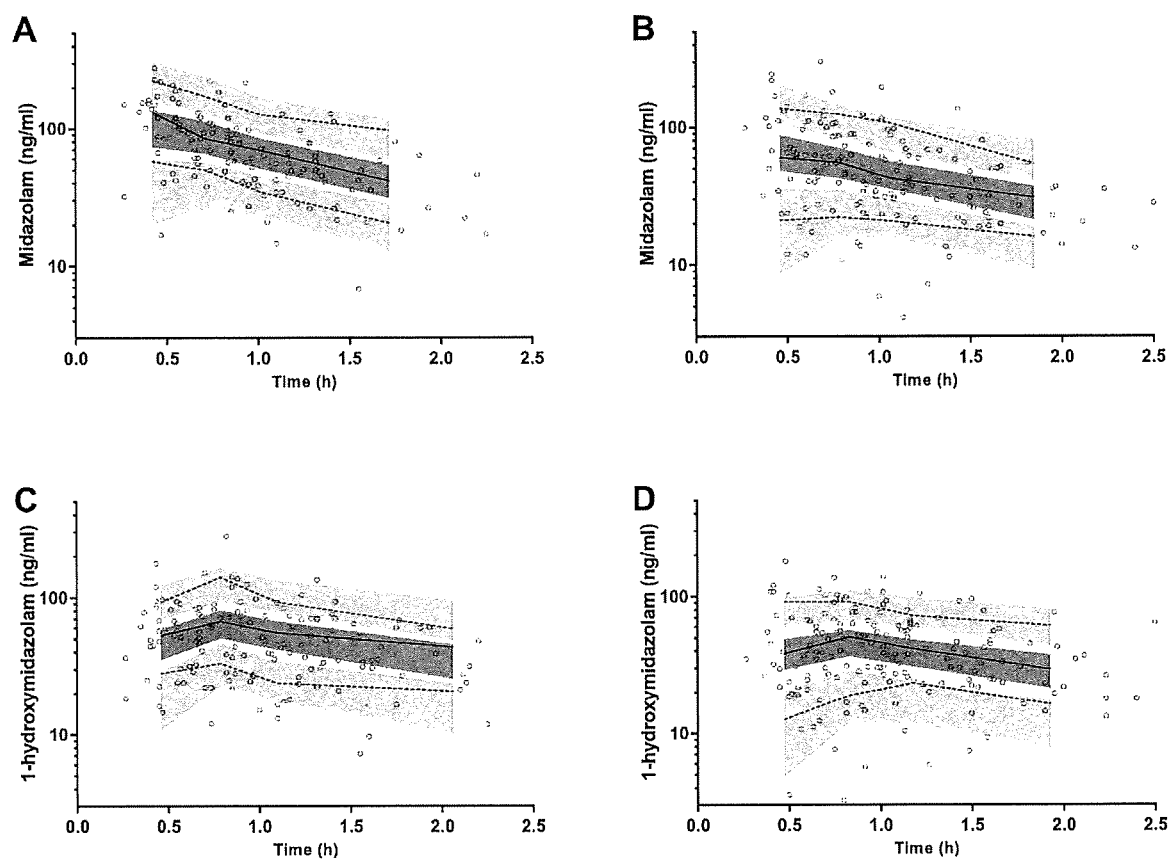
FIG. 8—Prediction corrected visual predictive check for midazolam (A, B) and 1-hydroxymidazolam (C, D) (ng/ml $\log_{10}$ scale) for children prior to surgery receiving oral midazolam either as IV formulation (A, C) or novel chocolate formulation (B, D). Plots demonstrate observed $50^{th}$ (solid line), $10^{th}$ and $90^{th}$ (dotted lines) percentiles within their simulated 95% CI (grey shaded areas) with overlying data points (○).
Figure 9:
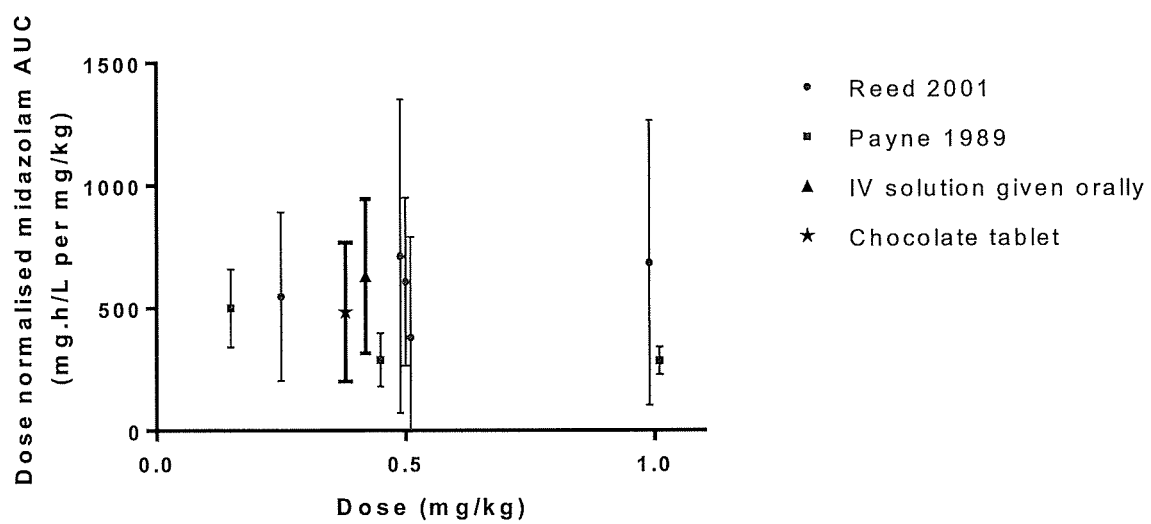
FIG. 9 Mean and standard deviation of dose normalized midazolam area under the curve for various dose levels in present and previously published reports (Reed M D, Rodarte A, Blumer J L, et al. The single-dose pharmacokinetics of midazolam and its primary metabolite in pediatric patients after oral and intravenous administration. *J Clin Pharmacol* 2001; 41: 1359-1369; Payne K, Mattheyse F J, Liebenberg D, et al. The pharmacokinetics of midazolam in paediatric patients. *Eur J Clin Pharmacol* 1989; 37: 267-272.)

Analysis of the mean visual analogue scale scores indicate a clear preference for the novel midazolam chocolate tablets compared to the IV midazolam solution administered orally (Table 2). There was significantly improved scoring on the 5-point scale for children, parent and clinical staff (all P<0.001), FIG. 7). This significant difference was noted across age and gender strata with at least P<0.05. Consistent with this, significantly more children in the chocolate group indicated they would take the formulation again if needed, 62% (chocolate tablet) vs. 39% (IV solution) (P=0.007).

Pharmacokinetic and Pharmacodynamic Data

Methods

Embedded in the clinical trial to evaluate the taste acceptance of the formulations in children was the study designed to determine the pharmacokinetic (PK) parameters and the bioavailability relative to comparator of the chocolate midazolam tablets.

Parents of patients recruited for the clinical study were asked whether they consented to having blood samples withdrawn from their child by the treating anaesthetist before, during and after anaesthesia. Informed consent was sought to have a separate IV cannula for the purpose of blood withdrawal. Approximately 3 mL of blood samples were collected from an IV cannula into heparin- or EDTA-coated tubes and labelled with the participant number and the time of collection. The first sample was collected as soon as possible after the child had fallen asleep (approximately 30 min or slightly earlier after taking midazolam). The second and third samples were collected between 45-60 min and 90-120 min, respectively. The final sample was collected as late as possible, before the procedure was completed. Blood samples were only collected when the child was asleep. Depending on the length of the procedure, up to four samples could be collected with total blood volume not exceeding 12 mL. Blood samples were processed to obtain plasma samples for HPLC analysis by centrifugation at 2000 g at 4° C. for 10 min. The plasma samples were transferred into Eppendorf tubes for storage at −80° C. until the HPLC analysis.

A validated HPLC assay was developed for the quantification of midazolam content in plasma. To prepare calibration standards, aliquots of 450 µL of human plasma were transferred into 15 mL screw-capped glass tubes and spiked with 30 µL each of midazolam and 1-hydroxymidazolam (primary metabolite) to give concentrations ranging from 0.2-5 µg/mL. Diazepam (30 µL of a 10 µg/mL solution) was added as internal standard. To prepare the test samples obtained from the trial subjects, aliquots of 450 µL of the patients' plasma samples were mixed with 30 µL of the 10 µg/mL diazepam solution (internal standard). Samples were then alkalinized with 20 µL of 0.5 M sodium hydroxide, and 4 mL of HPLC grade diethyl ether were added under vortex mixing for 10 min. The samples were centrifuged for 5 min at 1448 g at room temperature, then frozen at −40° C. for about 1 h. The organic layer was decanted into glass culture tubes and the diethyl ether was evaporated off under nitrogen gas to complete dryness. The residues were redissolved in 500 µL methanol under vortex for 30 s, and the extract was passed through a 0.2 µm×13 mm nylon syringe filter into a clean glass culture tube. The glass tubes were again rinsed with 400 µL of methanol and the vortexing and filtering processes repeated. The filtrates were combined and dried under nitrogen gas to complete dryness. The residues were then reconstituted in 100 µL of methanol, and 30 µL aliquots were immediately analysed in duplicates using the validated HPLC method. Midazolam and its 1-hydroxy metabolite were assayed by a reversed phase HPLC method using an Agilent Technologies 1260 Infinity HPLC (Agilent Technologies, Mulgrave, NSW, Australia) equipped with an autosampler and binary pump. Separation was carried out using a C18 column (ThermoFisher Scientific, BDS Hypersil C18, 5 µm, 250×4.6 mm) (Malaga, WA, Australia). The following gradient elution method was employed where solvent A was acetonitrile and solvent B was 20 mM potassium phosphate buffer at pH 5: A:B=35:65 graded to 45:55 (12 min), 45:55 (isocratic, 9 min), graded to 100:0 (7 min), 100:0 (isocratic, 5 min), graded to 35:65 (0.01 min), and finally 35:65 (isocratic 10 min). The flow rate was 1 mL/min. Midazolam (MDZ) and the 1-hydroxy metabolite (1OHMDZ) were detected at 245 nm.

The retention times for MDZ, 1OHMDZ and diazepam (internal standard) were 13.9, 10.2 and 17.0 min, respectively. Calibration curves for MDZ and 1OHMDZ were linear from 17 to 333 ng/ml ($R^2 \geq 0.99$). Inter- and intra-day accuracy and precision were suitable within this range with bias <9% and coefficient of variability <15%. The lower limit of quantification was 13 ng/ml for both analytes.

$Log_e$ plasma concentration-time datasets for MDZ and 1OHMDZ were analyzed by nonlinear mixed effects modeling using NONMEM (v 7.2.0, ICON Development Solutions, Ellicott City, Md., US) with an Intel Visual FORTRAN 10.0 compiler. A significance level of P<0.05 was set for comparison of nested models. Base models were parameterized using $V_C$ (central volume of distribution), CL (clearance), $V_P$ and Q (peripheral volumes of distribution and their respective inter-compartmental clearances). A time to event (onset of effect) was planned; this was not able to be established, attributable to a lack of concentration data prior to onset of effect.

Given the primary purpose of the analysis was to compare the two formulations, the novel chocolate formulation and the IV formulation given orally (the standard of care in our institution), different bioavailability and absorption parameters were estimated in the model. The bioavailability of the chocolate formulation relative to the IV formulation was included as a parameter while different absorption parameters for each of the formulations was included, where supported by the data.

Statistical analysis was performed using R version 2.14.2 (R Foundation for Statistical Computing, Vienna, Austria). Two-sample comparisons for non-normally distributed variables were by Mann Whitney U-test. Unless otherwise stated, all P-values are two-tailed and unadjusted for multiple comparisons.

Pharmacodynamic data (time to onset of sedation) was also collected for each participant to determine the clinical effect of midazolam, and this was recorded by the research nurse into the Patient Assessment Form.

Results

Pharmacodynamic Data

Of the 150 children recruited, 20 did not entirely ingest the first dose (12 in IV solution group, 6 in chocolate tablet group) and were excluded from the primary efficacy analysis. The time to onset of sedation was recorded for the 130 children who completely ingested the dose; this consisted of 62 in IV solution group and 68 in the chocolate tablet group. Except for the weight adjusted midazolam dose received, due to small difference in formulation dosing, there were no key differences in baseline characteristics between the IV solution and chocolate groups (Table 3).

TABLE 3

Baseline characteristics of children administered midazolam orally via an IV formulation or novel chocolate tablet included in the primary efficacy and PK analysis. Data presented as number (percentage) or median [interquartile range].

|  | IV solution formulation | Chocolate formulation | P value |
|---|---|---|---|
| Number | 62 | 67 (+1)[a] |  |
| Weight (kg) | 24 [19-40] | 24 [19-35] | 0.84 |
| Age (years) | 7.3 [4.6-10.2] | 6.7 [4.9-9.4] | 0.53 |
| Male | 28 (45) | 32 (48) | 0.77 |
| Height (cm) | 120 [110-137] | 120 [111-138][b] | 0.97 |
| Dose (mg of midazolam base) | 10.0 [8.8-15] | 9.0 [7.9-12.9] | 0.070 |
| Weight adjusted dose (mg/kg of midazolam base) | 0.47 [0.36-0.50] | 0.41 [0.30-0.45] | 0.0031 |

[a]One 6-year-old male with no evaluable PK data was included in the efficacy population but excluded from PK population; inclusion of this participant did not alter the between group comparisons presented.
[b]Height missing for one participant.

Despite a higher mg/kg dose in the IV solution group, there was no significant difference in the mean time to sedation onset observed for the IV solution group and the chocolate group (Table 4) (P=0.14). Additionally, the midazolam chocolate tablets achieved the clinical effect of sedation within 30 min of administration in all participants.

TABLE 4

The time to onset of sedation observed for children randomised to receive by oral administration midazolam IV solution and midazolam chocolate tablet

|  | Time to onset of sedation (min) Mean [interquartile range] |
|---|---|
| IV Solution Group (n = 62) | 11.5 [9-16] |
| Chocolate Group (n = 68) | 13.0 [10-17.5][a] |

[a]not significantly different from IV solution group (P = 0.14)

Behaviour scoring system was also used to evaluate children's behaviour after premedication in an interim data analysis (Table 5). While no children in the chocolate group (n=20) were scored 3 or 4, four children in the IV solution group (n=18) were scored 3 or 4 indicating insufficient anxiolysis.

TABLE 5

Behaviour scoring system

| Behaviour scoring | Behavioural Characteristics |
|---|---|
| 1 | Unafraid, calm, playing and relaxed |
| 2 | Calm with reassurance, suspicious |
| 3 | Miserable, afraid, anxious |
| 4 | Crying, clinging, combative |

Safety Evaluation

Both formulations were safe with no adverse events or severe adverse events observed during the study.

Pharmacokinetic Parameters

Of the 130 children, one participant in the chocolate group did not have any PK samples available and could not be included in the primary PK analysis. There were no key differences in baseline characteristics between the 62 participants in the IV solution group and 67 participants in the chocolate tablet group (Table 3).

Plasma MDZ and 1OHMDZ concentrations were analysed for 129 patients (n=62 for IV midazolam solution; n=67 for midazolam chocolate tablets; 294 time points). Population pharmacokinetic analysis was used to analyse the sparse sampling dataset. We were not able to calculate, or accurately simulate, the $C_{max}$ and $T_{max}$ values given the rapid absorption profile of midazolam. There was a clinical limitation of taking the first blood sample once a cannula had been placed after some effect of the pre-medication had taken place. Despite these limitations, the population model estimated a clinically insignificant trend for slower absorption in the chocolate tablet group with a mean transit time 2 minutes slower than the IV solution group. This is consistent with the pharmacodynamic data which also demonstrated a non-significant difference (Table 4).

Accounting for difference in absorption profile (including first-pass metabolism) between the two formulations, the relative bioavailability for the midazolam chocolate tablet group is estimated to be about 82% of the IV midazolam solution group (95% confidence intervals, 69-93%). The IV solution given orally appears to yield similar AUC to those reported in the literature for midazolam syrups. This would be consistent with the wide range of reported oral bioavailability for midazolam solid dosage forms (15-35%). The differences identified between the two formulations are not significant, particularly considering the comparison of a high concentration liquid to a solid form. Therefore, the chocolate based midazolam tablet did not affect the pharmacokinetics and bioavailability of the drug.

Observations

Of the 3 taste evaluation studies conducted for the novel midazolam chocolate tablets, the simplest and cheapest to perform were the in vitro dissolution experiments. There were no requirements for ethics approval and animal/patient recruitment. Provided the dissolution apparatus and drug assay equipment were available, consistent data could readily be obtained within days using as few as 3 replicate samples for each experiment.

Midazolam is a weak base ($pK_a$ 6.04). It is soluble in water (>2.5 mg/ml) at low pH, but its solubility decreased to less than 0.1 mg/ml at pH>5. In these studies, drug saturation (~0.004 mg/ml) was apparent within 10 min of introducing the midazolam chocolate tablet into the pH 6.8 simulated saliva medium. The absence of sink condition could underestimate drug release in the oral cavity in vivo. Conversely, the relative ease with which midazolam HCl dissolved in 0.1 M HCl would overestimate the amount of drug released into the mouth, as would the employment of 500 ml of dissolution medium. The typical saliva volume in human is less than 2 ml, but this low volume is difficult to apply in dissolution experiments.

These data suggest that the pre-crushing of tablet led to faster drug release in the first 30 min compared with the intact tablet, the cumulative drug released differing by 0.62 mg at t=0 and 1.79 mg at t=5 min.

Taste evaluation using the rat aversion model had the advantages of allowing the test dosage form to be simultaneously evaluated against a range of control samples, including blank vehicles. This permits a conclusion that the rats were less able to detect midazolam HCl when it was incorporated into the chocolate matrix than in the standard and syrup solutions. These data also provide calibration and taste thresholds for midazolam HCl, which is helpful for the formulation of taste masked products. On the basis that taste aversion was reflected by a significant reduction in the number of licks for a sample, it is possible to conclude that the detection threshold for the bitter taste of midazolam HCl was about 0.03 mg/ml in the rodent model. On this basis, and taking into consideration the in vitro drug release data and typical saliva volume, the chewable midazolam chocolate tablet may be extrapolated to release adequate amounts of drug into the oral cavity to elicit a bitter response in human.

Of the studies conducted on the midazolam chocolate tablets, the most direct taste data was obtained from the clinical trial involving paediatric patients aged 4 to 16, which also provided an analysis of pharmacodynamic effects in the target paediatric patients. The facial hedonic scales provided by the children suggest that the chocolate formulation was able to significantly mask the bitter taste of midazolam, as was the finding that 62% of the participants in the test group were willing to take the chocolate tablets again. The facial hedonic scores also suggest that not only the children, but the parents and nurses were all able to differentiate between the child's perception of the tastes of the midazolam chocolate tablet and solution.

The clinical taste data for the midazolam chocolate tablets correlated well with the rodent taste aversion data in showing the chocolate matrix was effective at masking the bitter taste of midazolam HCl. Corresponding data for the midazolam solution was less correlative. This solution was an IV midazolam injection available commercially. Its composition, which lacked flavour modulators, was similar to that of the midazolam standard solutions used in the rodent taste aversion experiments. However, while the rats were clearly averse to sipping the 1 mg/ml standard midazolam solution, many of the children were able to take the full dose of midazolam solution despite its 5-fold higher concentration. This could reflect a higher threshold tolerance for bitter taste in human than in rat, or the willingness of chronically sick children to take medications as a matter of routine regardless of the taste of the medication.

Example 2

The following provides an example for a formulation of Midazolam HCl 5 mg tablets:

| Midazolam HCl 5 mg tab | Quantity for 1 tab (500 mg tab) |
|---|---|
| midazolam hydrochloride | 5 mg |
| NaCl | 1 mg |
| Steviol | 2 mg |
| Xanthum gum | 5 mg |

| Midazolam HCl 5 mg tab | Quantity for 1 tab (500 mg tab) |
|---|---|
| Cremophor RH40 | 50 mg |
| PEG | 100 mg |
| dark choc | 404 mg |

In an alternate form of this formulation, NaCl may be removed altogether.

Example 3

The following provides an example for a formulation of Tramadol 10 mg tablets:

| Tramadol 10 mg tab | Quantity for 1 tab (500 mg tab) |
|---|---|
| tramadol hydrochloride | 11.3 mg |
| NaCl | 1 mg |
| Steviol | 2 mg |
| Xanthum gum | 5 mg |
| Cremophor RH40 | 50 mg |
| PEG | 100 mg |
| dark choc | 355 mg |
| flavour (orange) | 3 μl |

In an alternate form of this formulation, NaCl may be removed altogether.

Example 4

The following provides an example for a formulation of Clindamycin 37.5 mg tablets:

| Clindamycin 37.5 mg tab | Quantity for 1 tab (1 g tab) |
|---|---|
| clindamycin hydrochloride | 40.7 mg |
| NaCl | 2 mg |
| Steviol | 8 mg |
| Xanthum gum | 10 mg |
| Cremophor RH40 | 150 mg |
| PEG | 300 mg |
| dark choc | 598 mg |
| flavour (peach/raspberry) | 10 μl |

In an alternate form of this formulation, NaCl may be removed altogether.

Example 5

Clindamycin Hydrochloride Chocolate-Based Delivery System (CDS) Tablets

Clindamycin hydrochloride (HCl) is an antibiotic widely prescribed for paediatric patients for the treatment of middle ear infections, bone or joint infections, pelvic inflammatory disease, strep throat, pneumonia, and endocarditis among others. It can be useful against some cases of methicillin-resistant *Staphylococcus aureus*. Clindamycin HCl has been on the market since 1968, but the only registered oral product of clindamycin HCl in Australia is presented in the form of capsules. For paediatric patients who cannot safely swallow a capsule, the usual practice is for the caregivers to break open a capsule and mix all the capsule powder with water, juice or apple puree. It is unclear whether the pH of the juice or any kind of food with which the drug powder is mixed would have altered the stability of the drug. Moreover, clindamycin HCl has an extremely bitter taste that is well-documented in the literature. Children are particularly sensitive to the bitter taste, and these practices would not have effectively masked the drug taste, resulting in children reacting strongly to the aversive taste of clindamycin HCl. Poor compliance to the antibiotic is particularly problematic due to the potential of developing drug-resistant microbes.

Formulation of Clindamycin CDS Tablet

The clindamycin 37.5 mg CDS tablet was fabricated according to the formulation in Example 4.

Drug Content and Content Uniformity

Drug content in the tablets were determined by extracting clindamycin HCl from the tablet and determining the clindamycin HCl content by HPLC analysis. The CDS tablet was transferred into a tared 100 ml volumetric flask and weighed. Clindamycin HCl was extracted by adding 25 ml of methanol and 25 ml of deionized water, and heating the contents over a steam bath for 2-4 min (Rowe Scientific Pty, Ltd, Wangara, WA, Australia) with occasional agitation. Once the chocolate tablet had completely dissolved, 20 ml of methanol was added and the contents sonicated (Ultrasonic cleaner FXP08D, Unisonics Australia, Brookvale, NSW, Australia) for 2×1 min. The solution was allowed to cool before it was made up to 100 ml with methanol. An aliquot of the solution was filtered (0.45 μm nylon syringe filter, ThermoFisher Scientific, Malaga, WA, Australia) into an amber HPLC vial, and the clindamycin HCl content quantified using the HPLC assay.

In Vitro Drug Dissolution Profile

Protocol for the drug dissolution analysis for the clindamycin HCl CDS tablets was adapted and modified from the USP monograph for dissolution method described for clindamycin HCl capsules. The USP Apparatus 2 was used with the paddle rotating at 50 revolutions per minute (Varian VK 7010 Dissolution Apparatus, Agilent Technologies, Mulgrave, Victoria, Australia). The dissolution fluid was 900 ml of 0.1 M hydrochloric acid at 37° C. The dissolution medium was sampled at 0, 5, 10, 15, 30, 45 and 60 min. Aliquots of 1 mL were sampled at each time point, and filtered (0.45 μm) before injection into the HPLC for the assay of clindamycin HCl content. The dissolution experiments were performed in triplicate.

A simulated saliva medium (each 1 litre contained 8.00 g sodium chloride, 0.19 g potassium phosphate monobasic, and 2.38 g sodium phosphate dibasic, pH 6.8) was also used to evaluate drug dissolution from intact tablets (n=3). To reflect the smaller volume of saliva vs. gastric fluid in vivo, a volume of 300 mL was used, this being the minimum practical volume required for the USP dissolution apparatus. Aliquots were sampled from the dissolution medium at the same time points as that for the 0.1 M hydrochloric acid, and they were filtered (0.45 μm) prior to HPLC assay.

HPLC Analysis of Clindamycin HCl

Clindamycin HCl was quantified by reversed-phase high performance liquid chromatography on the Agilent 1260 Infinity binary pump HPLC system (Agilent Technologies Australia, Mulgrave, NSW, AUS) equipped with an BDS Hypersil C18 column (250 mm×4.6 mm, 5 μm particle size) from ThermoFisher Scientific (Malaga, WA, Australia). The HPLC method was adapted from the British Pharmacopoeia monograph for clindamycin HCl, testing for related substance. A gradient elution at a flow rate of 1.0 ml/min was employed, with clindamycin HCl detected at 210 nm. The mobile phase consisted of 35% v/v acetonitrile and 65% v/v potassium phosphate buffer (20 mM phosphate, pH 7.5) graded to 45% v/v acetonitrile in 8 min, then held at 45% v/v acetonitrile for another 8 min. Acetonitrile was then gradually increased to 80% v/v over 5 min and held at 80% v/v for 9 min before re-equilibrating to 35% v/v acetonitrile and 65% v/v phosphate buffer.

The HPLC was calibrated with standard solutions of clindamycin HCl (0 to 0.8 mg/ml) in methanol/water for the analysis of clindamycin HCl content in the chocolate tablet (n=3). To quantify clindamycin HCl in the dissolution media, the HPLC was calibrated with standard solutions of clindamycin HCl in 0.1 M HCl (0 to 80 μg/ml) and simulated saliva medium (0 to 200 μg/ml).

Taste Evaluation Data

A pilot, single centre, open label, randomised taste evaluation study was conducted to assess the acceptance of the clindamycin CDS tablet (37.5 mg clindamycin as clindamycin HCl in each 1×1×0.5 cm tablet) against a clindamycin oral solution (75 mg/5 ml of clindamycin as clindamycin HCl). The solution was extemporaneously compounded by a local pharmacy according to a proprietary formulation recently developed by the Professional Compounding Chemists of Australia (PCCA). It had the following formula: clindamycin 150 mg capsules×10, glycerol 6 ml, steviol glycosides (95%) 0.5 g, acesulfame potassium FCC 0.5 g, flavour marshmallow 2 ml, flavour raspberry 3 ml, flavour vanilla extract 1 ml, Medisca™ Oral Suspend 50 ml, Medisca™ Oral Syrup to 100 ml.

Participants of both gender, aged 18 to 25 years old, were recruited. Exclusion criteria were allergy to antibiotics or ingredients in the clindamycin CDS tablet or oral solution, pregnancy, breastfeeding, smoking, gastrointestinal diseases, feeling unwell or on medication.

All participants were required to read and sign the consent form. Each participant was given a dosing cup containing one clindamycin CDS tablet (equivalent to 37.5 mg clindamycin) and a separate dosing cup containing 2.5 ml of oral solution (equivalent to 37.5 mg clindamycin). The order of evaluation was randomised by a computer generated randomisation schedule for each participant. Participants cleansed their palate by drinking spring water and eating plain wafers prior to tasting the first formulation. They were instructed to evaluate the tablet by using a chew and spit method, and the solution by a swill and spit method. After 10 s of chewing/swilling, the participants were instructed to spit the contents into a cup provided. They were provided spring water and plain wafers to remove residual taste, and instructed to evaluate the second formulation after a 10 min wash-out period.

Participants were asked to record how much they like each formulation immediately after tasting both formulations by marking on separate five-point facial scales. Participants were also asked to indicate which one of the two formulations they would be willing to take again if they become sick and clindamycin is required.

Results

Calibration of HPLC

Figure 10:
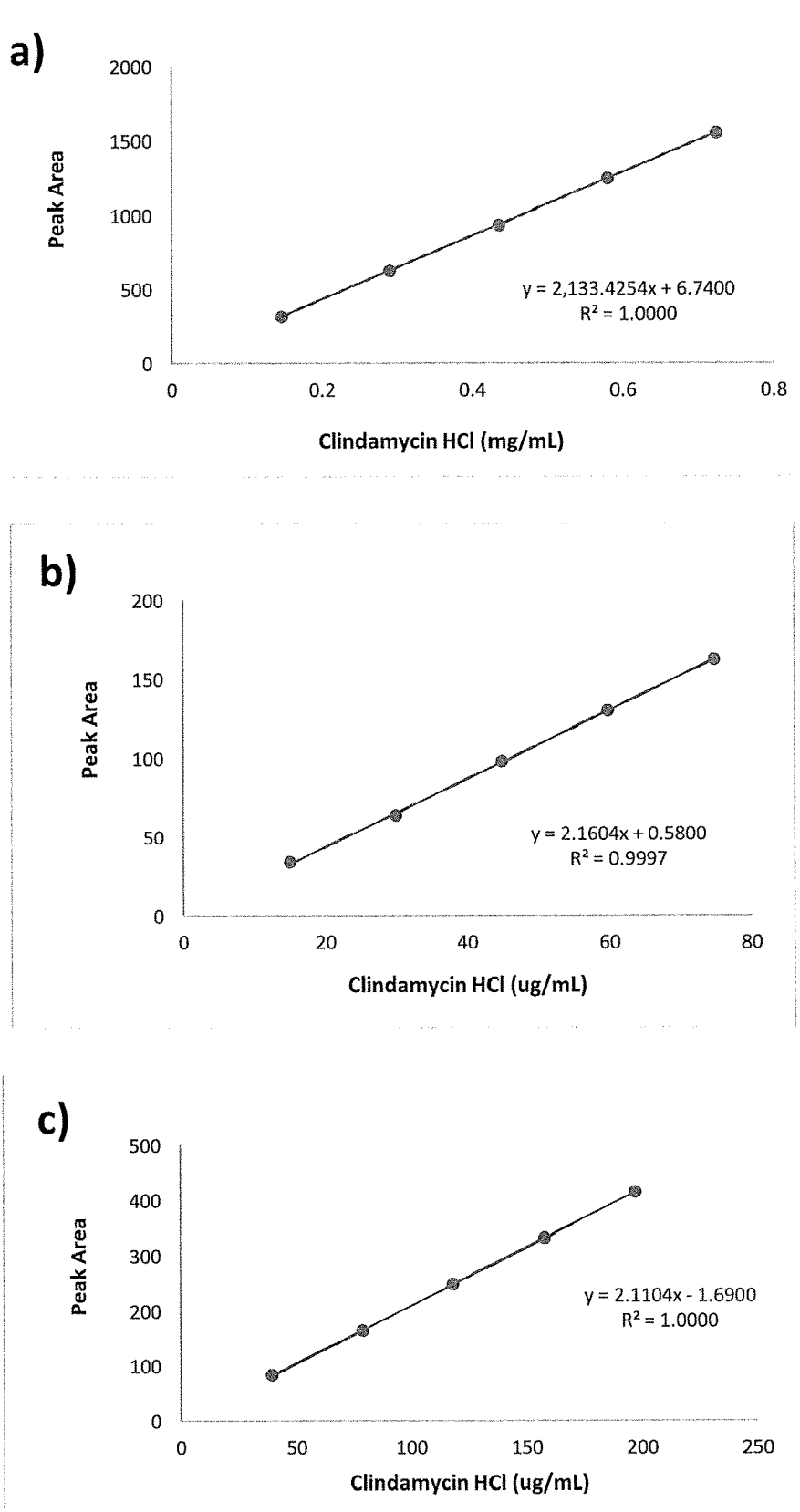
FIG. 10 Standard curves of clindamycin HCl in (a) methanol/water, (b) 0.1 M HCl and (c) simulated saliva medium. Linear calibration curves were obtained for the standard solutions of clindamycin HCl in methanol/water (FIG. 10a), 0.1 M HCl (FIG. 10b) and simulated saliva medium, pH 6.8 (FIG. 10c).

Linear calibration curves were obtained for the standard solutions of clindamycin HCl in methanol/water (FIG. 10a), 0.1 M HCl (FIG. 10b) and simulated saliva medium, pH 6.8 (FIG. 10c).

Drug Content and Stability Data

Figure 11:
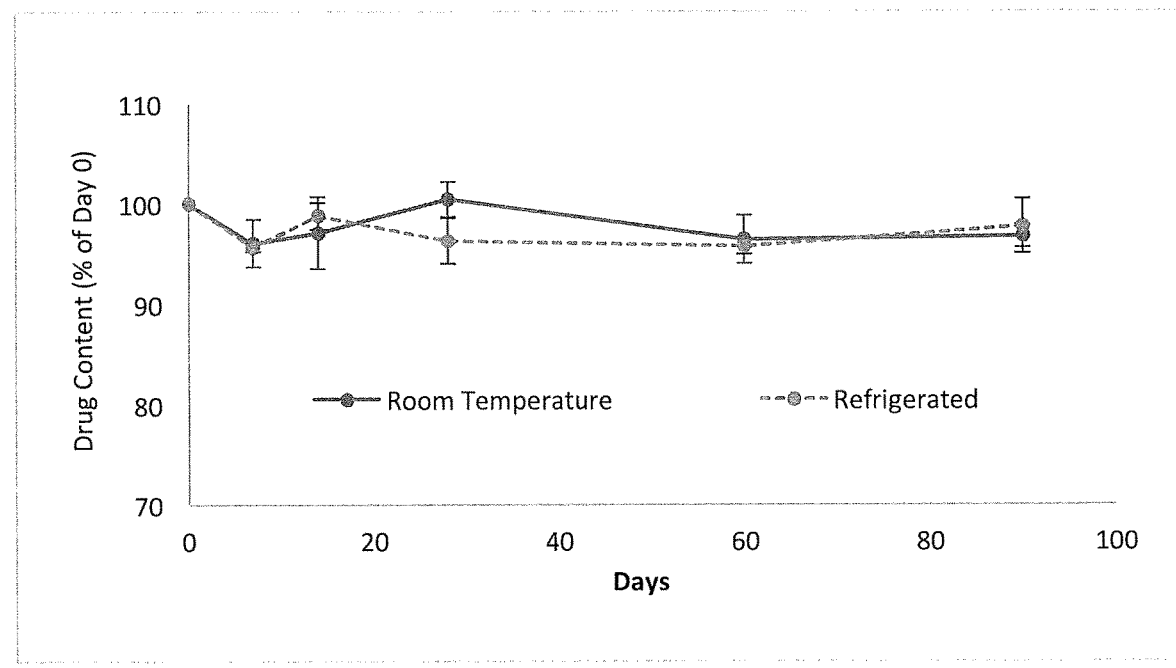
FIG. 11 Residual drug content as a function of storage time for clindamycin HCl CDS tablets stored wrapped in foil at refrigerated and ambient temperatures.
Figure 12:
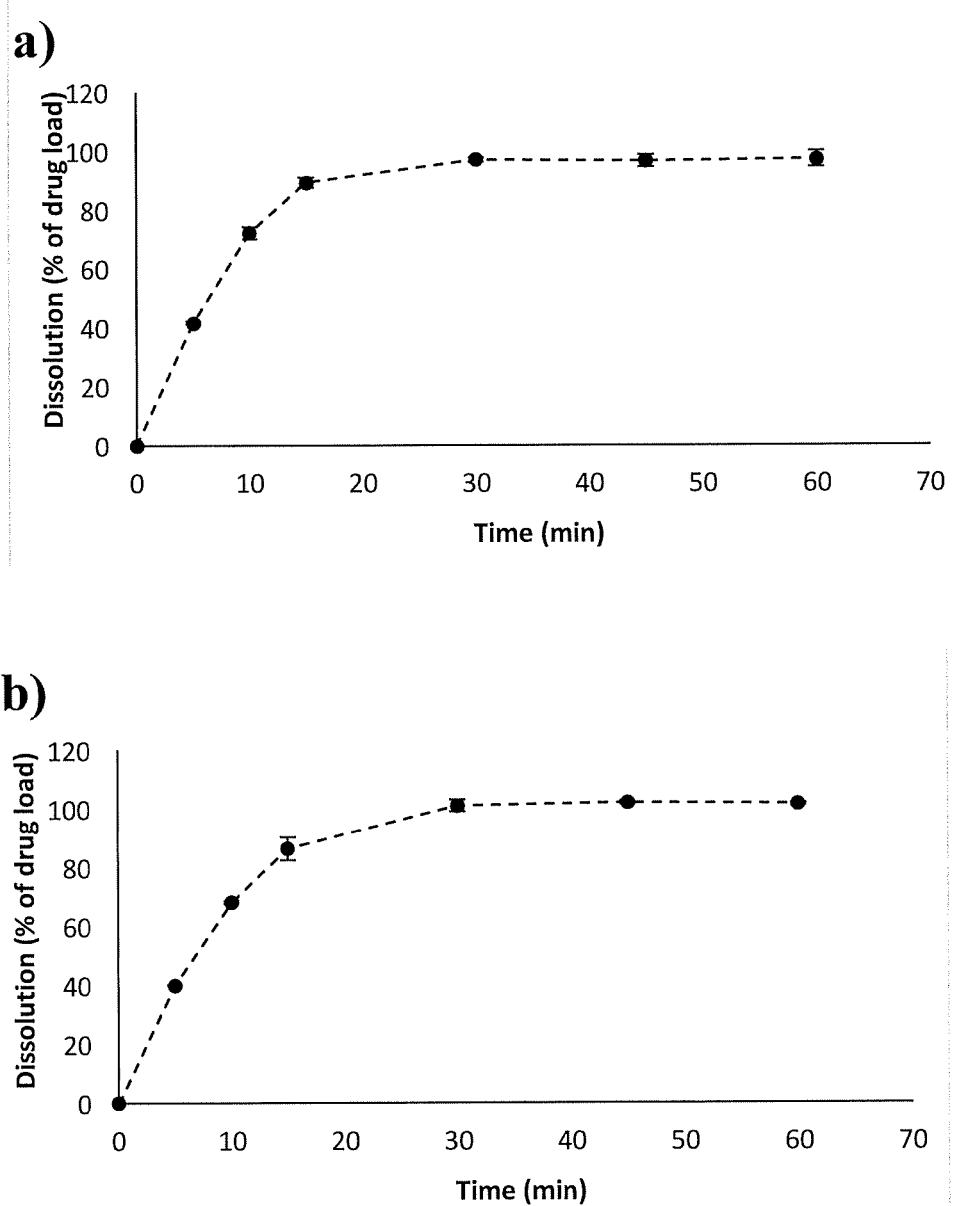
FIG. 12 In vitro drug dissolution profile of clindamycin HCl CDS tablets in (a) 0.1 M HCl and (b) simulated saliva medium. Data represent mean±SD, n=3.

Drug content analysis suggests the tablets contained 100.2±2.05% of labelled drug strength (n=3), which was within the 95-105% requirement based on US Pharmacopoeia specifications. The drug was stable during manufacture and after at least 3 months storage at refrigerated and ambient temperatures, the residual drug content was 97.8% and 96.8% (n=3), respectively (See FIG. 11).

In Vitro Dissolution Data

The United States Pharmacopoeia (USP) monograph for clindamycin HCl capsules stipulates not less than (NLT) 80% of the clindamycin HCl content should dissolve in 30 min, while the British Pharmacopoeia (BP) stipulates NLT 70% dissolution of the clindamycin content in 45 min. Our data showed that, in both 0.1M HCl and simulated saliva, there was approximately 100% dissolution of the clindamycin HCl content from the intact chocolate tablet in 30 min. Therefore, the intact CDS tablets showed compliance with the pharmacopoeia standards even in this medium, with more than 80% dissolution of the clindamycin HCl content in 15 min. Thus, the clindamycin CDS tablets were deemed to have complied with the USP and BP standards for dissolution of clindamycin HCl capsules.

Taste Evaluation Study

A total of 16 participants took part in the taste evaluation study. Each participant evaluated both the clindamycin CDS tablet and oral solution in one sitting, and the order of evaluation was randomised.

Compared with midazolam CDS tablet and tramadol CDS tablet, the clindamycin CDS tablet scored lower in the 5-point scale, which is a reflection of the higher drug content in the tablet and the more challenging taste characteristics of clindamycin HCl. However, the clindamycin CDS tablet was no worse in taste compared to the syrup-based extemporaneous oral solution (Table 6) (p=0.63, paired Student's t-test). One participant did not show a clear preference for either formulation while 9 would prefer to take the oral solution and 6 would take the tablet if they become sick and require clindamycin.

TABLE 6

Taste scores given by 16 participants aged 18 to 25 years old for the clindamycin HCl CDS tablet and oral solution.

| Formulation | Clindamycin chocolate tablet | Clindamycin oral solution |
|---|---|---|
| Taste score (mean ± SD, n = 16) | 1.84 ± 1.26 | 2.00 ± 0.89 |

Although the two formulations are similar in taste, the clindamycin HCl CDS tablet is superior to the clindamycin HCl oral solution in not requiring refrigerated storage, having a longer shelf life and offering greater dosing convenience and accuracy to patients (Table 7).

TABLE 7

Comparisons between clindamycin chocolate tablet and PCCA clindamycin oral solution

| Formulation | Clindamycin chocolate tablet | Clindamycin oral solution |
|---|---|---|
| Storage conditions | Ambient OR refrigerated temperatures | Only refrigerated temperature |
| Shelf life | At least 3 months (stability data still being collected) | 1 month |
| Convenience to patient | Very convenient to take (chewable and no need for water) and transport | Require accurate measurement into dosing cup for administration. More inconvenient to transport |
| Dosing accuracy | Accurate dosing is readily achievable | Requires accurate measurement of volume using a dosing cup, which can be stressful for caregivers trying to administer a poor tasting liquid |

Example 6

Tramadol Chocolate-Based Delivery System (CDS) Tablets

Pain specialists are frustrated by the limited availability of approved potent analgesics for children undergoing surgery and cancer therapy. Paracetamol does not induce strong analgesia, and there are concerns over NSAIDS causing bleeding, asthma exacerbation and renal impairment, while opioid use is associated with respiratory depression. Tramadol, a centrally acting codeine analog with less potential for abuse and a better safety profile than oxycodone, is prescribed widely for treating moderate and severe pain in adults. However, none of the 82 registered tramadol products on the Australian Register of Therapeutic Goods is recommended for use in children, despite several clinical trials showing tramadol to be effective and safe in managing paediatric pain.

Almost all of the registered oral tramadol products are presented as tablets and capsules. Only one product is an oral liquid which, if not for its high concentration (100 mg/ml) and therefore high risk of accidental overdosing, may have provided young patients with a tramadol product that is easy to swallow. Doctors in Australia are, however, strongly advised against prescribing the tramadol oral drops for children under 12 following the death of a 2 year-old child from accidental overdosing. The oral drops present significant safety risks to young patients because only very small dose volumes are required, which not only make accurate measurement an onerous task, but the high drug concentration compounds inaccuracy in measured volumes to give potentially fatal doses. Diluting the oral drops with water is not a recommended clinical practice. The oral drops contain co-solvents and solubilizers; the addition of water can potentially destabilize the product by increasing vehicle polarity and reducing the solubilising capacity that then lead to the precipitation of drug particles.

Consequently, the off-label use of tramadol will have to be met by manipulating the capsule and tablet products into powder or liquid doses to ease administration in young children. Pain specialists at the Princess Margaret Hospital/Perth Children's Hospital in Perth are reluctant to prescribe a drug that is not available in an appropriate paediatric formulation. At the Royal Children Hospital (RCH) in Melbourne, caregivers and nurses are provided with a leaflet containing instructions on how to transform a 50 mg tramadol HCl capsule into a 5 mg/ml oral liquid for children under their care.6, 9 This manipulation is required for every dose prescribed, making it a highly tedious practice. More importantly, despite the detailed instructions, which reflect the potential risks involved, the administered dose will only be as accurate as the extent of care with which the caregivers take to accurately measure the water, open the capsule without spilling its contents, empty the entire capsule content into the water with adequate stirring to ensure uniformity, and then, before the insoluble powders had a chance to settle, quickly syringing out an accurate volume for the patient. This multi-step exercise can add considerable stress to the caregivers and regularly exposes them to the drug, yet for all their efforts, the end product is unpalatable. The solubility of tramadol HCl in aqueous media is no higher than 2 mg/ml, and the drug has an extremely bitter taste, with low detection threshold of 20 micrograms/ml in adults. With the removal of the barrier (capsule shell) that blocks drug release and access to taste receptors in the oral cavity, and children being generally more sensitive to bitter taste, the paediatric tramadol doses (1-2 mg/kg/dose every 4-6 h) delivered via this method is almost invariably highly unpalatable. Poor adherence to therapy is the persistent factor interrupting the continuum of care for many paediatric patients.

Methods

Formulation

Tramadol CDS tablet was fabricated in accordance with the formulation given in Example 3.

Drug Content and Storage Stability

Drug content in the tablets were determined by extracting tramadol HCl from the tablet and determining the tramadol HCl content by HPLC analysis. The CDS tablet was cut into 8 pieces, transferred into a 100-ml volumetric flask, and weighed to determine the weight of the tablet. Tramadol HCl was extracted from the tablet by adding 25 ml of methanol and 15 ml of deionized water, and heating the contents over a steam bath for 2 min (Rowe Scientific Pty, Ltd, Wangara, WA, Australia) with occasional agitation. Once the CDS tablet had completely dissolved, 50 ml of methanol was added and the contents sonicated (Ultrasonic cleaner FXP08D, Unisonics Australia, Brookvale, NSW, Australia) for 2×1 min. The solution was allowed to cool before it was made up to 100 ml with methanol. An aliquot of the solution was filtered (0.45 µm nylon syringe filter, ThermoFisher Scientific, Malaga, WA, Australia) into an amber HPLC vial, and the tramadol HCl content quantified using the HPLC assay.

Tablets were individually wrapped in foil and stored in ointment jars at ambient temperature immediately after manufacture. At specified time points, 3 tablets were removed from storage and examined for changes in gross morphology. The tramadol content for each tablet was determined and expressed as the percent residual tramadol HCl based on the drug content determined on the day of manufacture.

In Vitro Drug Dissolution Profile

Protocol for drug dissolution analysis of the tramadol HCl CDS tablets was adapted from the FDA guidelines for tramadol HCl tablets (200 mg). The USP Apparatus 2 was used with the paddle rotating at 100 revolutions per minute (Varian VK 7010 Dissolution Apparatus, Agilent Technologies, Mulgrave, Victoria, Australia). The dissolution fluid was 450 ml of 0.1 M hydrochloric acid at 37° C.; the volume applied was lower than the 900 ml stipulated in the USP/FDA guidelines because of the lower tramadol HCl content (10 mg) in the CDS tablets. The dissolution medium was sampled at 0, 5, 10, 20, 30, 45 and 60 minutes, and the aliquots were filtered (0.45 µm) before injection into the HPLC for the assay of tramadol content. The dissolution experiments were performed in triplicate. Parallel experiments to mimic the chewing of tablets in the oral cavity were conducted by crushing the CDS tablets (n=3) with a pestle prior to the dissolution experiments.

A simulated saliva medium (8.00 g/L sodium chloride, 0.19 g/L potassium phosphate monobasic, and 2.38 g/L sodium phosphate dibasic, pH 6.8) was also used to evaluate drug dissolution from intact (n=3) and crushed (n=3) tablets. To reflect the smaller volume of saliva vs. gastric fluid in vivo, a volume of 300 mL was used, this being the minimum practical volume of medium to be used with the USP dissolution apparatus. Aliquots were sampled of the dissolution medium at 0, 2, 5, 10, 20, 40 and 60 minutes, and filtered (0.45 µm) prior to HPLC assay for tramadol HCl content.

HPLC Analysis of Tramadol HCl

Tramadol HCl was quantified by reversed-phase high performance liquid chromatography on an Agilent 1260 Infinity binary pump HPLC system (Agilent Technologies Australia, Mulgrave, NSW, AUS) equipped with an Xbridge C18 column (100 mm×4.6 mm, 5 µm particle size) from Waters Australia Pty Ltd (Rydalmere, NSW, AUS). A gradient elution at a flow rate of 0.8 ml/min was employed, with tramadol HCl detected at 270 nm. The mobile phase consisted of 20% v/v acetonitrile and 80% v/v potassium phosphate buffer (20 mM phosphate, pH 6.0) graded to 80% acetonitrile in 6 min, then held at 80% acetonitrile for another 2 min before re-equilibrating to 20% acetonitrile and 80% phosphate buffer in 4 min.

The HPLC was calibrated with standard solutions of tramadol HCl dissolved in methanol/water (0 to 200 µg/ml) for the determination of tramadol HCl content in the tablets, and with standard solutions of tramadol HCl in 0.1 M HCl (0 to 180 µg/ml) and simulated saliva medium (0 to 60 µg/ml) for the determination of drug dissolution profiles of the tablets.

Taste Evaluation

Preliminary taste evaluation was conducted with 22 participants who each took 4 tramadol CDS tablets: unflavoured, flavoured with orange or flavoured with banana essence. Each participant was asked to give a score based on the 5-point facial score chart.

Results

Calibration of HPLC

Figure 13:
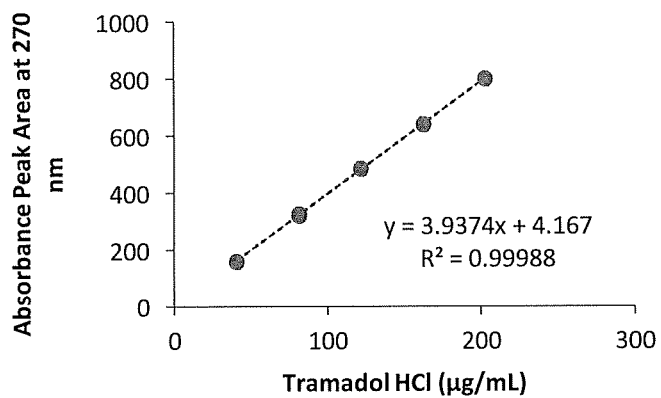
FIG. 13 Standard curve of tramadol HCl in (a) methanol/water, (b) 0.1 M HCl and (c) simulated saliva medium.
Figure 13:
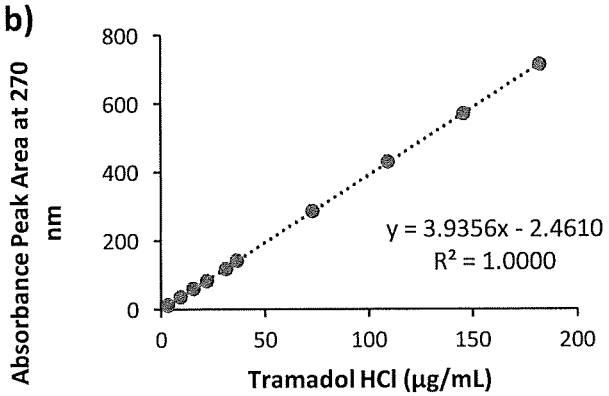
Figure 13:
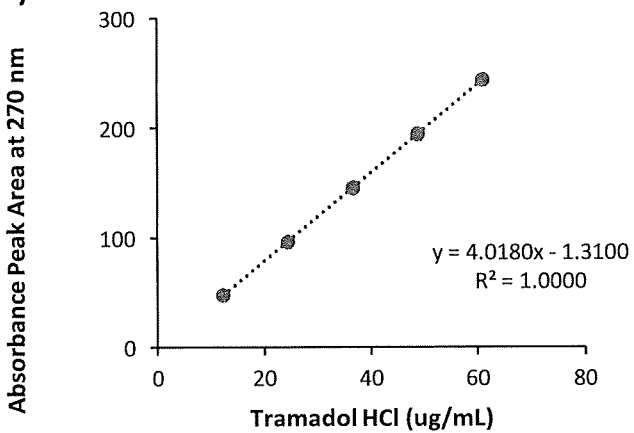

Linear calibration curves were obtained for the standard solutions of tramadol HCl in methanol/water (FIG. 13a), 0.1 M HCl (FIG. 13b) and simulated saliva medium, pH 6.8 (FIG. 13c).

Tramadol HCl Content of CDS Tablet

The measured tramadol HCl (mw 299.84) content of the CDS tablet was 11.35±0.03 mg (n=3). This was equivalent to 9.97 mg tramadol base (mw 263.4), and 98.5% of the labelled drug content. The tramadol CDS tablet therefore conforms to the USP monograph for drug content of tramadol HCl tablets (95-105% labelled content).

Storage Stability

Figure 14:
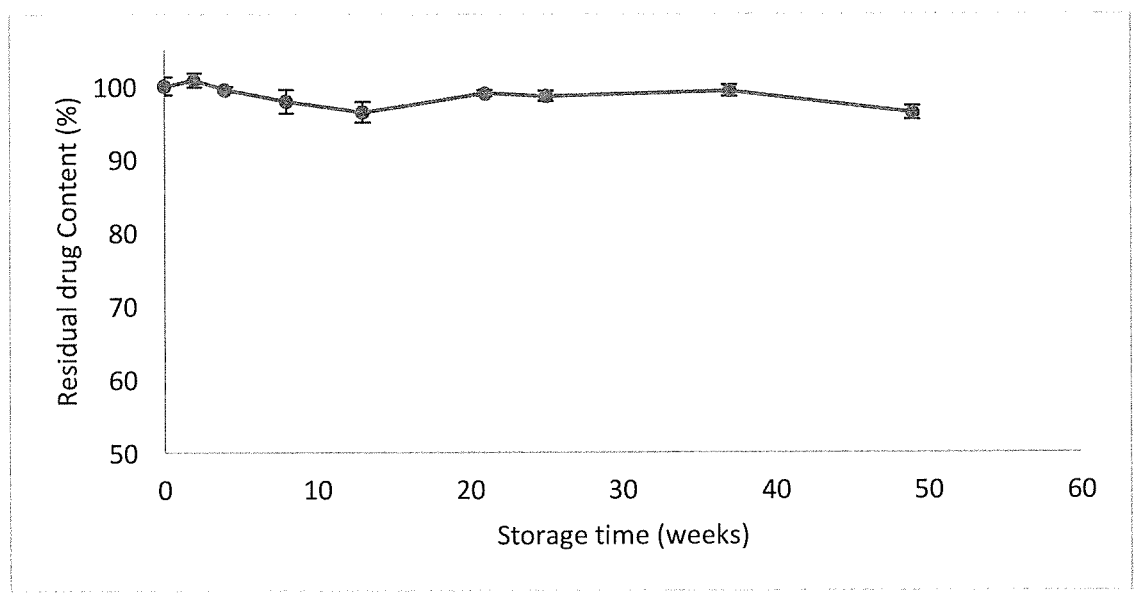
FIG. 14 Residual tramadol content as a function of storage time for tramadol HCl CDS tablets stored wrapped in foil at ambient temperature.

The tramadol HCl CDS tablet has been found to be stable for at least 49 weeks when stored wrapped in foil at ambient temperature. At 49 weeks, the residual tramadol HCl content in the tablet was 96.3±0.85% (n=3) (FIG. 14).

Dissolution Profiles of Tramadol HCl CDS Tablets

Figure 15:
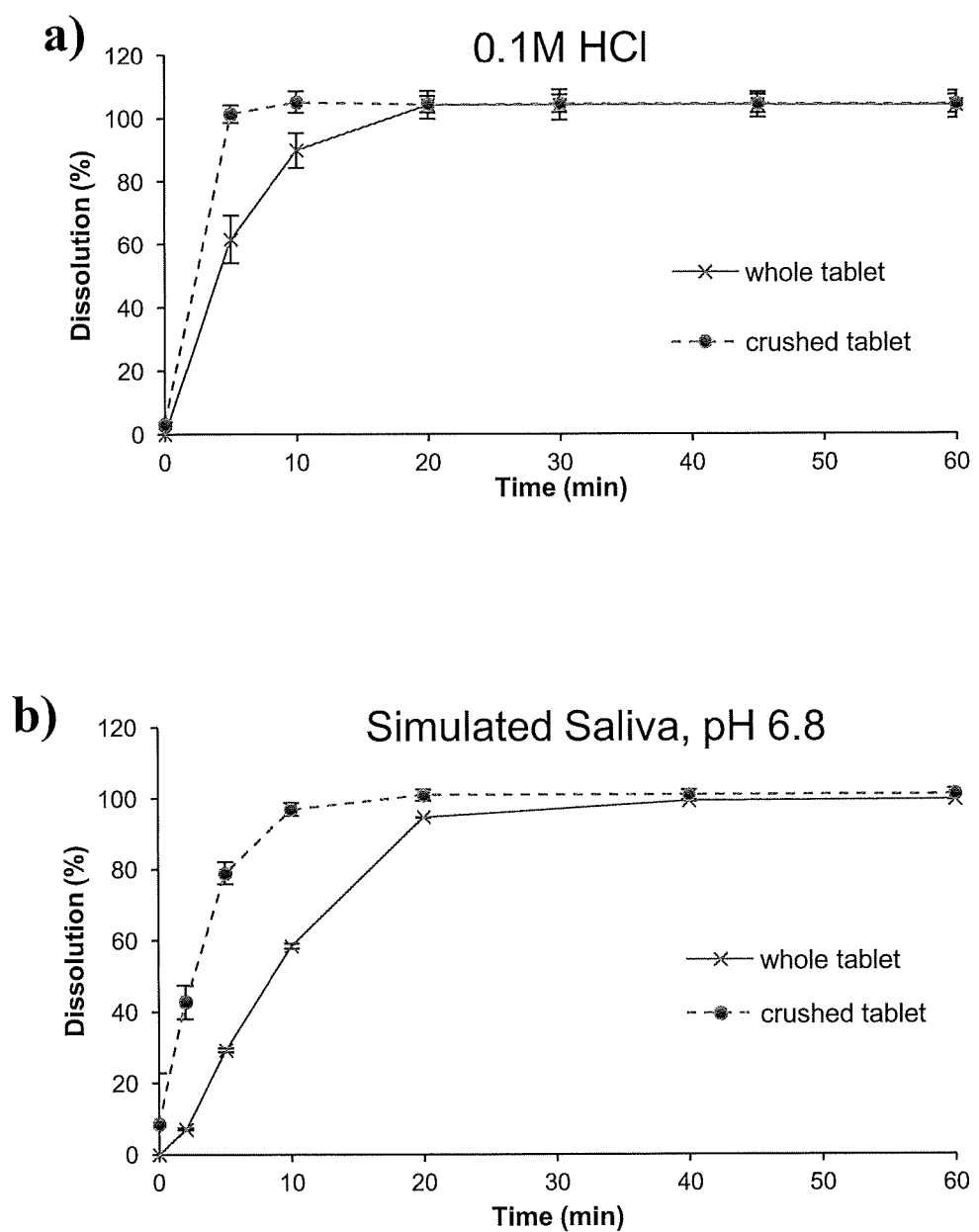
FIG. 15 In vitro drug dissolution profiles for tramadol HCl CDS tablets in (a) 0.1 M HCl and (b) simulated saliva medium (♦—intact tablets; ×—crushed tablets). Data represent mean±SD, n=3.

The United States Pharmacopoeia (USP) monograph for tramadol HCl tablets stipulates not less than (NLT) 80% of the tramadol HCl content should dissolve in 30 min, while the British Pharmacopoeia (BP) stipulates NLT 70% dissolution of the tramadol content in 45 min. Our data showed that, in 0.1M HCl, there was complete (100%) dissolution of the tramadol content in 20 min for the intact CDS tablet, and a faster rate of drug dissolution, 100% in 5 min, for the crushed tablets (n=3). (see FIG. 15)

When the dissolution medium was changed to 300 mL of simulated saliva, there was a slower dissolution of tramadol from the CDS tablet, particularly in the first 5 min. This augers well for the peroral administration of the tablets, as it implied a slower and smaller amount of the bitter drug would be released into the oral cavity. Nonetheless, both the intact and crushed tablets showed compliance with the pharmacopoeia standards even in the simulated saliva medium, with more than 80% of the tramadol content dissolving in 20 min. Thus, the tramadol CDS tablets are deemed to have complied with the USP and BP standards for dissolution of tramadol HCl tablets.

Taste Evaluation

To determine whether the addition of a flavouring essence to the base tramadol CDS tablet formulation would enhance its taste acceptance, a total of 22 participants took part in the taste evaluation of the unflavoured and flavoured tramadol CDS tablet. The taste scores are summarized in Table 8. The tramadol CDS tablet formulation that was flavoured with orange essence attracted the highest mean taste score, and this was significantly higher than the mean scores given for the unflavoured formulation, but was not different from the mean score for the banana-flavoured formulation. The orange-flavoured tramadol 10 mg CDs tablet was chosen as the final formulation.

TABLE 8

Taste scores given by 22 participants for tramadol CDS tablet that was unflavoured, and flavoured with banana and orange essence.

| Flavouring added | None | Banana | Orange |
|---|---|---|---|
| Taste score on 5-point scale (Mean ± SD, n = 22) | 2.38 ± 1.02 | 3.00 ± 1.23 | 3.50 ± 0.91[a] |

[a]significantly different from unflavoured, but not different from banana flavoured formulations (one-way ANOVA, p < 0.05)

The invention claimed is:

1. A chewable chocolate or chocolate substitute composition or product comprising:
   (a) at least an active ingredient to be delivered to a subject, wherein the active ingredient comprises a pharmaceutical compound or drug or a nutritional compound, mineral, vitamin, or herb;
   (b) a compound or dark chocolate, wherein the compound or dark chocolate comprises at least 40% cocoa mass or dark chocolate substitute mass;
   (c) a masking agent that masks at least part of the taste of the active ingredient in (a) wherein the masking agent comprises one or more hydrogenated ethoxylated glycerol esters;
   (d) a suspending agent wherein the suspending agent comprises xanthan gum; and
   (e) a firming agent wherein the firming agent comprises polyethylene glycol (PEG);
   wherein the composition or product (i) is prepared in the absence of water and (ii) is substantially stable at ambient temperature, such that the composition or product is capable of being stored for at least 4 months at ambient temperature while preserving greater than 70% activity of the active ingredient of (a).

2. The chewable composition or product according to claim 1, wherein the compound or dark chocolate comprises 40% to 70% cocoa mass or dark chocolate substitute mass.

3. The chewable composition or product according to claim 1, wherein the masking agent comprises one or more hydrogenated ethoxylated castor oils.

4. The chewable composition or product according to claim 1, wherein the compound or dark chocolate comprises 45% cocoa mass or dark chocolate substitute mass.

5. The chewable composition or product according to claim 1, wherein the masking agent is present in an amount of about 5 to 20 percent dry weight of the final composition, the suspending agent is present in an amount of about 0.01 to 10 percent dry weight of the final composition, and the firming agent is present in an amount of about 5 to 25 percent dry weight of the final composition.

6. The chewable composition or product according to claim 1, wherein the firming agent is an emulsifying or solubilizing agent for the active ingredient in (a).

7. The chewable composition or product according to claim 1, wherein the composition or product comprises:
   (a) the active ingredient to be delivered to a subject;

(b) the compound or dark chocolate wherein the compound or dark chocolate comprises at least 40% cocoa mass or dark chocolate substitute mass;
(c) a Cremophor;
(d) xanthan gum; and
(e) a PEG.

8. The chewable composition or product according to claim 7, wherein the Cremophor is present in an amount of about 5 to 20 percent dry weight of the final composition, xanthan gum is present in an amount of about 0.01 to 10 percent dry weight of the final composition and the PEG is present in an amount of about 5 to 25 percent dry weight of the final composition.

9. The chewable composition or product according to claim 1, wherein the active ingredient of (a) is a bitter or unpleasant tasting active pharmaceutical compound.

10. The chewable composition or product according to claim 9, wherein the bitter or unpleasant tasting active pharmaceutical compound is a sedative, anxiolytic, analgesic, or an antibiotic.

11. The chewable composition or product according to claim 9, wherein (i) the bitter or unpleasant tasting active pharmaceutical compound is midazolam or a salt thereof, or midazolam hydrochloride, or tramadol or a salt thereof, or tramadol hydrochloride, or clindamycin or clindamycin hydrochloride.

12. A method of preparing the chewable chocolate or chocolate substitute composition or product of claim 1, wherein the method includes the steps of:
    a) mixing the active ingredient to be delivered to the subject and the masking agent and/or the suspending agent to produce a homogenous mixture;
    b) combining the mixture of step (a) with the firming agent;
    c) combining the mixture of step (b) with the chocolate or chocolate substitute,
    wherein step (c) is performed for at least 4 hours to ensure that a substantially homogenous product is produced,
    wherein the composition or product (i) is prepared in the absence of water and (ii) is substantially stable at ambient temperature, such that the composition or product is capable of being stored for at least 4 months at ambient temperature while preserving greater than 70% activity of the active ingredient of (a).

13. The method of preparing the chewable chocolate or chocolate substitute composition or product of claim 12, wherein the method includes the steps of:
    a) mixing midazolam hydrochloride or tramadol hydrochloride, Cremophor RH40, steviol glycoside, and xanthan gum, and optionally sodium chloride, using a stirrer hot plate set at about 55° C. until homogeneously dispersed;
    b) combining polyethylene glycol to the mixture of step (a) and mixing;
    c) combining the chocolate or chocolate substitute to the mixture of (b), stirring to melt and mixing until fully incorporated;
    wherein the mixture of step (c) is then mixed for a further 16 hours to produce a homogeneous product.

14. The chewable composition or product according to claim 1, wherein the compound or dark chocolate substitute is carob or cocoa powder comprising at least 40% carob or cocoa powder mass, respectively.

15. The chewable composition or product according to claim 1, wherein the composition or product comprises the compound or dark chocolate in an amount of at least 50% of the total weight of the composition or product.

16. The method according to claim 13, wherein the method comprises mixing the active ingredient of midazolam hydrochloride in step (a).

17. The chewable composition or product according to claim 7, wherein the Cremophor in part (c) is PEG-40 hydrogenated castor oil (Cremophor RH40), and/or wherein the PEG in part (e) is PEG 1450; and optionally wherein the chewable composition or product further comprises steviol glycoside and optionally sodium chloride.

18. The chewable composition or product according to claim 1, wherein the firming agent adds structure to the compound or dark chocolate and assists in emulsifying or solubilizing the active ingredient of (a).

19. The chewable composition or product according to claim 1, wherein the active ingredient in (a) is selected from sedatives and anxiolytics, analgesics, antibiotics, antiparasitic, antiviral, anti-inflammatory drugs, or wormwood herb.

* * * * *